United States Patent [19]

Beavo et al.

[11] Patent Number: 5,652,131
[45] Date of Patent: Jul. 29, 1997

[54] CYCLIC GMP-BINDING, CYCLIC GMP-SPECIFIC PHOSPHODIESTERASE MATERIALS AND METHODS

[75] Inventors: Joseph A. Beavo, Seattle, Wash.; Jackie D. Corbin, Nashville, Tenn.; Kenneth M. Ferguson, Bothell, Wash.; Sharron H. Francis, Nashville, Tenn.; Ann Kadlecek; Kate Loughney, both of Seattle, Wash.; Linda M. McAllister-Lucas, Nashville, Tenn.; William K. Sonnenburg, Mountlake Terrace, Wash.; Melissa K. Thomas, Boston, Mass.

[73] Assignees: ICOS Corporation, Bothell, Wash.; Vanderbilt University, Nashville, Tenn.; Board of Regents of the University of Washington, Seattle, Wash.

[21] Appl. No.: 480,547

[22] Filed: Jun. 7, 1995

Related U.S. Application Data

[63] Continuation of Ser. No. 68,051, May 27, 1993, abandoned.
[51] Int. Cl.$^6$ .............. C12N 15/55; C12N 9/16; C12N 15/63; C12N 1/21
[52] U.S. Cl. .......... 435/196; 536/23.1; 536/23.2; 536/23.5; 435/69.1; 435/320.1; 435/172.3; 435/252.3; 435/325; 435/70.1; 435/70.3; 435/71.1; 435/71.2; 435/252.33; 435/254.2; 435/365; 935/3; 935/14; 935/27; 935/28; 935/29; 935/56; 935/69; 935/70; 935/72; 935/73
[58] Field of Search .................... 536/23.1, 23.2, 536/23.5; 435/196, 69.1, 320.1, 172.3, 252.3, 240.2, 70.1, 70.3, 71.1, 71.2, 252.33, 254.2; 935/3, 14, 27, 28, 29, 56, 69, 70, 72, 73

[56] References Cited

FOREIGN PATENT DOCUMENTS

WO 92/18541 10/1992 WIPO.
WO 93/05182 3/1993 WIPO.

OTHER PUBLICATIONS

Ausubel et al., *Current Protocols in Molecular Biology*, John Wiley & Sons, New York (1987) [Table of Contents].
Beavo et al., *Cyclic Nucleotide Phosphodiesterases: Structure, Regulation and Drug Action*, John Wiley & Sons, Chichester, UK (1990) [Table of Contents].
Bradford, "A Rapid and Sensitive Method for the Quantitation of Microgram Quantities of Protein Utilizing the Principle of Protein–Dye Binding", *Anal. Biochem.*, 72:248–254 (1976).
Charbonneau et al., "Identification of a Noncatalytic cGMP–Binding Domain Conserved in Both the cGMP–Stimulated and Photoreceptor Cyclic Nucleotide Phosphodiesterases", *Proc. Natl. Acad. Sci. USA*, 87:288–292 (1990).

Charbonneau, "Structure–Function Relationships Among Cyclic Nucleotide Phosphodiesterases", Chapter 11, pp. 267–296 in Beavo et al., *Cyclic Nucleotide Phosphodiesterases: Structure, Regulation and Drug Action*, John Wiley & Sons, Chichester, UK (1990).
Collins et al., "The Human β–Subunit of Rod Photoreceptor cGMP Phosphodiesterase:Complete Retinal cDNA Sequence and Evidence for Expression in Brain", *Genomics*, 13:698–704 (1992).
Coquil et al., "Characteristics of a New Binding Protein Distinct From the Kinase for Guanosine 3':5'–Monophosphate in Rat Platelets", *Biochim. Biophys. Acta*, 631:148–165 (1980).
Coquil et al., "Occurance of the Methylisobutylxanthine–Stimulated Cyclic GMP Binding Protein in Various Rat Tissues", *Biochem. Biophys. Res. Commun.*, 127:226–231 (1985).
Davis et al., "Purification and Characterization of Guanosine 3':5'–Monophosphate–specific Phosphodiesterase from Guinea Pig Lung", *J. Biol. Chem.*, 252:4078–4084 (1977).
Dayhoff et al., "Establishing Homologies in Protein Sequences", *Methods Enzymol.*, 92:524–545 (1983).
Erickson et al., "Macromolecular X–Ray Crystallography and NMR as Tools for Structure–based Drug Design", *Ann. Rep. Med. Chem.*, 27:271–289 (1992).
Feinberg et al., "A Technique for Radiolabeling DNA Restriction Endonuclease Fragments to High Specific Activity", *Anal. Biochem.*, 137:266–267 (1984).
Feng et al., "Progressive Alignment and Phylogenetic Tree Construction of Protein Sequences", *Methods Enzymol.*, 183:375–387 (1990).
Flockhart et al., "Preparation of the Catalytic Subunit of cAMP–Dependent Protein Kinase", Chapter 12, pp. 209–215 in Marangos et al., *Brain Receptor Methodologies*, Part A, Academic Press, Orlando, Florida (1984).
Francis et al., "Cyclic GMP–Binding Cyclic GMP–Specific Phosphodiesterase from Lung", Chapter 5, pp. 117–140 in Beavo et al., *Cyclic Nucleotide Phosphodiesterases: Structure, Regulation and Drug Action*, John Wiley & Sons, Chichester, UK (1990).
Francis et al., "Characterization of a Novel cGMP Binding Protein from Rat Lung", *J. Biol. Chem.*, 255:620–626 (1979).
Francis et al., "Purification of cGMP–Binding Protein Phosphodiesterase from Rat Lung", *Methods Enzymol.*, 159:722–729 (1988).
Hamet et al., "Cyclic GMP Binding and Phosphodiesterase: Implication for Platelet Function", *Adv. Cyclic Nucleotide Protein Phosphorylation Res.*, 16:119–136 (1984).

(List continued on next page.)

Primary Examiner—Rebecca E. Prouty
Attorney, Agent, or Firm—Marshall, O'Toole, Gerstein, Murray & Borun

[57] ABSTRACT

The present invention provides novel purified and isolated nucleotide sequences encoding the cGMP-binding, cGMP-specific phosphodiesterase designated cGB-PDE. Also provided by the invention are methods and materials for the recombinant production of cGB-PDE polypeptide products and methods for identifying compounds which modulate the enzymatic activity of cGB-PDE polypeptides.

12 Claims, 10 Drawing Sheets

OTHER PUBLICATIONS

LeTrong et al., "Amino Acid Sequence of the Cyclic GMP Stimulated Cyclic Nucleotide Phosphodiesterase from Bovine Heart", *Biochemistry*, 29:10280–10288 (1990).

Li et al., "Bovine Cone Photoreceptor cGMP Phosphodiesterase Structure Deduced from A cDNA Clone", *Proc. Natl. Acad. Sci. USA*, 87:293–297 (1990).

Lipkin et al., "β–Subunit of Bovine Rod Photoreceptor cGMP Phosphodiesterase", *J. Biol. Chem.*, 265:12955–12959 (1990).

Martins et al., "Purification and Characterization of a Cyclic GMP–Stimulated Cyclic Nucleotide Phosphodiesterase from Bovine Tissues", *J. Biol. Chem.*, 257:1973–1979 (1982).

Matsudaira, "Sequence from Picomole Quantities of Proteins Electroblotted Onto Polyvinylidene Difluoride Membranes", *J. Biol. Chem.*, 262:10035–10038 (1987).

Murray et al., "Inhibitors of Cyclic Nucleotide Phosphodiesterases as Therapeutic Agents", *Biochem. Soc. Trans.*, 20(2):460–464 (1992).

Oskenberg et al., "A Single Amino–Acid Difference Confers Major Pharmacological Variation Between Human and Rodent 5–HT$_{1B}$ Receptors", *Nature*, 360:161–163 (1992).

Ovchinnikov et al., "Cyclic GMP Phosphodiesterase from Cattle Retina", *FEBS Lett.*, 204:288–292 (1986).

Ovchinnikov et al., "Cyclic GMP Phosphodiesterase From Bovine Retina", *FEBS Lett.*, 223:169–173 (1987).

Reeves et al., "Cardiac Phosphodiesterases and the Functional Effects of Selective Inhibition," Chapter 12, pp. 300–316 in Beavo et al., *Cyclic Nucleotide Phosphodiesterases: Structure, Regulation and Drug Action*, John Wiley & Sons, Chichester, UK (1990).

Sonnenburg et al., "Molecular Cloning of a Cyclic GMP–Stimulated Cyclic Nucleotide Phosphodiesterase cDNA", *J. Biol. Chem.*, 266:17655–17661 (1991).

Thomas et al., "Substrate– and Kinase–directed Regulation of Phosphorylation of a cGMP–binding Phosphodiesterase by cGMP", *J. Biol. Chem.*, 265:14971–14978 (1990).

Thomas et al., "Characterization of a Purified Bovine Lung cGMP–Binding cGMP Phosphodiesterase", *J. Biol. Chem.*, 265:14964–14970 (1990).

Wilbur et al., "Rapid Similarity Searches of Nucleic Acid and Protein Data Banks", *Proc. Natl. Acad. Sci. USA*, 80:726–730 (1983).

E. Uhlmann et al. "Antisense Oligonucleotides:A New Therapeutic Principle" Chem. Reviews. 90(4)543–584 (Jun. 1990).

K.J. Murray et al. "Inhibitors of cyclic nucleotide Phosphodiesleases as therapeutic Agents" Biochem. Soc. Trans. 20: 460–464 (1992).

W. K. Sonnenburg et al. "Molecular Cloning of a Cyclic GMP–Stimulated Cyclic Nucleotide Phosphodieterase cDNA" J. Biol Chem. 266(26)17655–17661 (Sep. 1991).

M. K. Thomas. et al "Characterization of a Purified Bovine Lung cGMP..." J. Biol Chem. 265(25) 14964–14970 (Sep. 1990).

M.K. Thomas et al. "Substrate and Kinase–directed Regulation . . . " J. Biol. Chem. 265(25) 14971–14978 (Sep. 1990).

M.P. Deutscher (ed.) "Guide to Protein Purification" Meth. in Enzeymol. vol. 182 pp. 602–613, 738–751 (1990).

| | | | | | |
|---|---|---|---|---|---|
| CGB-PDE | FQMKHEVLCK | WILSVKKNYR | K.NVAYHNWR | HAFNTAQCMF | AALKAGKIQK | 626 |
| ROS-α | FHIPQEALVR | FMYSLSKGYR | R..ITYHNWR | HGFNVGQTMF | SLLVTGKLKR | 582 |
| ROS-β | FQIPQEVLVR | FLFSVSKGYR | R..ITYHNWR | HGFNVAQTMF | TLLMTGKLKS | 580 |
| CONE-α' | FKVPVEVLTR | WMTYVRKGYR | A..VTYHNWR | HGFNVGQTMF | TLLMTGRLKK | 580 |
| CGS | YKIDCPTLAR | FCLMVKKGYR | D.P.PYHNWM | HAFSVSHFCY | LLYKNLELTN | 659 |
| 61 KCAM | FKIPVSCLIA | FAEALEVGYS | KYKNPYHNLI | HAADVTQTVH | YIMLHTGIMH | 242 |
| 63 KCAM | FKIPTVFLMT | FLDALETGYG | KYKNPYHNQI | HAADVTQTVH | CFLLRTGMVH | 244 |
| Ratdunce | FQIPADTLLR | YLLTLEGHYH | S.NVAYHNSI | HAADVVQSAH | VLLGTPALEA | 125 |
| Drosdunce | .MIPPKTFLN | FMSTLEDHYV | K.DNPFHNSL | HAADVTQSTN | VLLNTPALEG | 48 |
| Conserved | ----*---- | -------- | ----HN-* | H-----* | -----* | |

| | | | | | |
|---|---|---|---|---|---|
| CGB-PDE | RLTDLEILAL | LIAALSHDLD | HRGVNNSYIQ | RSEHPLAQLY | CH..SIMEHH | 674 |
| ROS-α | YFTDLEALAM | VTAAFCHDID | HRGTNNLYQM | KSQNPLAKLH | GS...SILERH | 630 |
| ROS-β | YYTDLEAFAM | VTAGLCHDID | HRGTNNLYQM | KSQNPLAKLH | GS...SILERH | 628 |
| CONE-α' | YYTDLEAFAM | LAAAFCHDID | HRGTNNLYQM | KSTSPLARLH | GS...SILERH | 628 |
| CGS | YLEDMEIFAL | FISCMCHDLD | HRGTNNSFQV | ASKSVLAALY | SSEGSVMERH | 709 |
| 61 KCAM | WLTELEILAM | VFAAAIHDYE | HIGTTNNFHI | QTRSDVAILY | .NDRSVLENH | 291 |
| 63 KCAM | CLSEIEVLAI | IFAAAIHDYE | HIGTTNSFHI | QTKSEQAILY | .NDRSVLENH | 293 |
| Ratdunce | VFTDLEVLAA | IFACAIHDVD | HPGVSNQFLI | NTNSELALMY | .NDSSVLENH | 174 |
| Drosdunce | VFTPLEVGGA | LFAACIHDVD | HPGLTNQFLV | NSSSELALMY | .NDESVLENH | 97 |
| Conserved | ---E---- | -------- | H-G----- | ----*-A--- | ----S--E-H | |

FIGURE 1A

| | | | | | |
|---|---|---|---|---|---|
| CGB-PDE | HFDQCLMILN | SPGNQILSGL | SIEEYKTTLK | IIKQAILATD | LALYIKRRGE | 714 |
| ROS-α | HLEFGKTLLR | DESLNIFQNL | NRRQHEHAIH | MMDIAIIATD | LALYCKKRTM | 680 |
| ROS-β | HLEFGKFLLS | EETLNIYQNL | NRRQHEHVIH | LMDIAIIATD | LALYFKKRTM | 678 |
| CONE-α' | HLEYSKTLLQ | DESLNIFQNL | NKRQYETVIH | LFEVAIIATD | LALYFKKRTM | 678 |
| CGS | HFAQAIAILN | THGCNIFDHF | SRKDYQRMLD | LMRDIILATD | LAHHLRIFKD | 748 |
| 61 KCAM | HVSAAYRLMQ | EEEMNVLINL | SKDDWRDLRN | LVIEMVLSTD | MSGHFQQIKN | 326 |
| 63 KCAM | HISSVFRMMQ | DDEMNIFINL | TKDEFVELRA | LVIEMVLATD | MSCHFQQVKS | 328 |
| Ratdunce | HLAVGFKLLQ | GENCDIFQNL | STKQKLSLRR | MVIDMVLATD | MSKHMSLLAD | 220 |
| Drosdunce | HLAVAFKLLQ | NQGCDIFCNM | QKKQRQTLRK | MVIDIVLSTD | MSKHMSLLAD | 143 |
| Conserved | H-------- | ---------- | ---------- | -------TD | --**-*-*-- | |

| | | | | | |
|---|---|---|---|---|---|
| CGB-PDE | FFELIMKN.. | ........QF | NLEDPHQKEL | FLAMLMTACD | LSAITKPWPI | 764 |
| ROS-α | FQKIVDQSKT | YETQQEWTQY | MMLDQTRKEI | VMAMMMTACD | LSAITKPWEV | 730 |
| ROS-β | FQKIVDESKN | YEDRKSWVEY | LSLETTRKEI | VMAMMMTACD | LSAITKPWEV | 728 |
| CONE-α' | FQKIVDACEK | METEEEAIKY | VTIDPTKKEI | IMAMMMTACD | LSAITKPWEV | 728 |
| CGS | LQKMAE... | ......VGY | DRTNKQHHSL | LLCLLMTSCD | LSDQTKGWKT | 798 |
| 61 KCAM | IRNSLQQPEG | L......... | ......DKAK | TMSLILHAAD | ISHPAKSWKL | 376 |
| 63 KCAM | MKTALQQLER | I......... | ......DKSK | ALSLLLHAAD | ISHPTKQWSV | 378 |
| Ratdunce | LKTMVETKKV | T....SLGVL | LLDNYSDRIQ | VLQSLVHCAD | LSNPAKPLPL | 270 |
| Drosdunce | LKTMVETKKV | A....GSGVL | LLDNYTDRIQ | VLENLVHCAD | LSNPTKPLPL | 193 |
| Conserved | *--------- | ---------- | ---------* | ------D | -S**-K--- | |

FIGURE 1B

|  |  |  |  |  |  |
|---|---|---|---|---|---|
| cGB-PDE | QQRIAELVAT | EFFDQGDRER | KELNIEPADL | MNREKKNKIP | SMQVGFID.. | 812 |
| ROS-α | QSKVALLVAA | EFWEQGDLER | TVLQQNPIPM | MDRNKADELP | KLQVGFID.. | 778 |
| ROS-β | QSKVALLVAA | EFWEQGDLER | TVLDQQPIPM | MDRNKAAELP | KLQVGFID.. | 776 |
| CONE-α' | QSQVALLVAN | EFWEQGDLER | TVLQQQPIPM | MDRNKKDELP | KLQVGFID.. | 776 |
| CGS | TRKIAELIYK | EFFSQGDLEK | A.MGNRPMEM | MDREKAY.IP | ELQISFME.. | 844 |
| 61 KCAM | HHRWTMALME | EFFLQGDKEA | EL..GLPFSP | LCDRKSTMVA | QSQIGFID.. | 422 |
| 63 KCAM | HSRWTKALME | EFFRQGDKEA | EL..GLPFSP | LCDRTSTLVA | QSQIGFID.. | 424 |
| Ratdunce | YRQWTERIMA | EFFQQGDRER | ES..GLDISP | MCDKHTASVE | KSQVGFID.. | 316 |
| Drosdunce | YKRWVALLME | EFFLQGDKER | ES..GMDISP | MCDRHNATIE | KSQVGFID.. | 239 |
| Conserved | *----**- | EF--QGD-E- | ---------- | ---------- | --Q--F--- | |

FIGURE 1C

```
CGB-PDE     LLELVKDISS HLDVTALCHK IFLHIHGLIS ADRYSLFLVC EDSSNDKFLI  188
CGS         ILQLCGELYD .LDASSLQLK VLQYLQQETQ ASRCCLLLVS EDN..LQ.LS  245
CONE-α'     LLEVL..LEE AGSVELAAHR ALQRLAQLLQ ADRCSMFLCR ARNGTPE.VA  106
ROS-β       LFELVQDMQE NVNMERVVFK ILRRLCSILH ADRCSLFMYR QRNGVAE.LA  107
ROS-α       ...LLRDFQD NLQAEKCVFN VMKKLCFLLQ ADRMSLFMYR ARNGIAE.LA  109
CONSERVED   ---------- ---------- ---------- A-R------- ----------

CGB-PDE     SRLFDVAEGS TLEE...ASN NCIRLEWNKG IVGHVAAFGE PLNIKDAYED  237
CGS         CKVIG...DK VLEE...... .EISFPLTTG RLGQVVEDKK SIQLKDLTSE  292
CONE-α'     SKLLDVTPTS KFEDNLVVPD REAVFPLDVG IVGWAHTKK  TFNVPDVKKN  154
ROS-β       TRLFSVQPDS VLEDCLVPPD SEIVFPLDIG VVGHVAQTKK MVNVQDVMEC  155
ROS-α       TRLFNVHKDA VLEECLVAPD SEIVFPLDMG VVGHVALSKK IVNVPNTEED  157
CONSERVED   ---------- ------E--- ---------G --G-V----- ----------

CGB-PDE     PRFNAEVDQI TGYKTQSILC MPIKNHR.EE VVGVAQAINK KSGNGGTFTE  287
CGS         DM..QQLQSM LGCEVQAMLC VPVISRATDQ VVALACAFNK ..LGGDLFTD  342
CONE-α'     SHFSDFMDKQ TGYVTRNLLA TPIV..MGKE VLAVFMAVNK ..VDASEFSK  204
ROS-β       PHFSSFADEL TDYVTRNILA TPIM..NGKD VVAVIMAVNK ..LDGPCFTS  205
ROS-α       EHFCDFVDTL TEYQTKNILA SPIM..NGKD VVAIIMAVNK ..VDGPHFTE  207
CONSERVED   ---------- ------L--- ---P------ V-----A-NK ------F---
```

FIGURE 2A

```
CGB-PDE      KDEKDFAAYL  AFCGIVLHNA  QLYETSLLEN  KRNQVLLDLA  SLIFEEQQSL   337
CGS          QDEHVIQHCF  HYTSTVLTST  LAFQKEQKLK  CECQALLQVA  KNLFTHLDDV   390
CONE-α'      QDEEVFSKYL  SFVSIILKLH  HTNYLYNIES  RRSQILMWSA  NKVFEELTDV   252
ROS-β        EDEDVFLKYL  NFGTLNLKIY  HYSYLHNCET  RRGQVLLWSA  NKVFEELTDI   253
ROS-α        NDEEILLKYL  NFANLIMKVF  HLSYLHNCET  RRGQILLWSG  SKVFEELTDI   255
CONSERVED    -DE-------  ----------  ----------  ---Q--L---  ---F------

CGB-PDE      EVILKKIAAT  IISFMQVQKC  TIFIVD.EDC  SDSFSSVFHM  ECEELEKSSD   361
CGS          SVLLQEIITE  ARNLSNAEIC  SVFLID...Q  NELVAKVFDG  GVLEDESY..   409
CONE-α'      ERQFHKALYT  VRTYLNCERY  SIGLLDMTKE  KEFY.DEWPV  KPGEVEPYKG   301
ROS-β        ERQFHKAFYT  VRAYLNCDRY  SVGLLDMTKE  KEFF.DVWPV  LMGEAQAYSG   302
ROS-α        ERQFHKALYT  VRAFLNCDRY  SVGLLDMTKQ  KEFF.DVWPV  LMGEAPPYAG   304
CONSERVED    ----------  ----------  ------D---  ----------  ---E------

CGB-PDE      TLTRE.....  ..........  .RDANRINY   MYAQYVKNTM              411
CGS          ..........  ..........  .PADQ....   GIAGHVATTG              459
CONE-α'      PKTPDGREVI  FYKIIDYILH  .EIRI....   GKEEIKVIPT  PPMDHWTLIS  GLPTYVAENG  351
ROS-β        PRTPDGREIL  FYKVIDYILH  GKEDIKVIPS  PPADHWALAS  GLPTYVAESG              352
ROS-α        PRTPDGREIN  FYKVIDYILH  GKEDIKVIPN  PPPDHWALVS  GLPTYVAQNG              354
CONSERVED    ----------  ----------  ------D---  ----------  ---V------
```

FIGURE 2B

```
cGB-PDE     EPLNIPDVSK  DKRFPWTNEN  MGNINQQCIR  SLLCTPIKNG  KKNKVIGVCQ   459
cGS         QILNIPDAYA  HPLFY..RGV  DDSTGRF.TR  NILCFPIKN.  ENQEVIGVAE   499
CONE-α'     FICNMLNAPA  DEYFTFQKGP  VDETGWV.IK  NVLSLPIVN.  KKEDIVGVAT   399
ROS-β       FICNIMNAPA  DEMFNFQEGP  LDDSGWI.VK  NVLSMPIVN.  KKEEIVGVAT   400
ROS-α       LICNIMNAPS  EDFFAFQKEP  LDESGWM.IK  NVLSMPIVN.  KKEEIVGVAT   402
CONSERVED   ---N------  ---F------  ----------  --L--PI-N-  -----GV-- cGB-PDE     LVNKMEETTG  KVKAFNRNDE  QFLEAFVIFC  GLGIQNTQMY  EAVERAMAKQ   506
cGS         LVNKING...  ..PWFSKFDE  DLATAFSIYC  GISIAHSLLY  KKVNEAQYRS   541
CONE-α'     FYNRKDG...  ..KPFDEYDE  HIAETLTQFL  GWSLLNTDTY  EKMNKLENRK   441
ROS-β       FYNRKDG...  ..KPFDEQDE  VLMESLTQFL  GWSVLNTDTY  DKMNKLENRK   442
ROS-α       FYNRKDG...  ..KPFDEMDE  TLMESLAQFL  GWSVLNPDTY  ELMNKLENRK   444
CONSERVED   ---N------  ----F---DE  ----------  G-------Y  ---------- cGB-PDE     MVTLEVLSYH  ASAAEEE                                          526
cGS         HLANEMMMYH  MKVSDDE                                          561
CONE-α'     DIAQEMLMNH  TKATPDE                                          461
ROS-β       DIAQDMVLYH  VRCDREE                                          462
ROS-α       DIFQDMVKYH  VKCDNEE                                          464
CONSERVED   --------H  -----E
```

FIGURE 2C

```
CGB-PDE    A   EPLNIKDAYEDPRF...NAEVDQITGYKTQSILCMPIKMH.REEVVGVAQAIN.KKSGN
ROS-α      A   KIVNVPNTEEDEHF...CDFVDTLTEYQTKNILASPIMNG.K.DVVAIIMAVN.KVDGP
ROS-β      A   KMVNVQDVMECPHF...SSFADELTDYVTRNILATPIMNG.K.DVVAVIMAVN.KLDGP
CONE-α'    A   KTFNVPDVKKNSHF...SDFMDKQTGYVTRNILATPIVMG.K.EVLAVFMAVN.KVDAS
CGS        A   KSIQLKDLTSEDM.....QQLQSMLGCEVQAMLCVPVISRATDQVVALACAFN.KLGGD
CGB-PDE    B   EPLNIPDVSKDKRFPWTNENMGNINQQCIRSLLCTPIKNGKNKVIGVCQLVN.KMEET
ROS-α      B   LICNIMNAPSEDFFAFQKEPLDE.SGWMIKNVLSMPIVNK.KEEIVGVATFYNRKDGKP
ROS-β      B   FICNIMNAPADEMFNFQEGPLDD.SGWIVKNVLSMPIVNK.KEEIVGVATFYNRKDGKP
CONE-α'    B   FICNMLNAPADEYFTFQKGPVDE.TGWVIKNVLSLPIVNK.KEDIVGVATFYNRKDGKP
CGS        B   QILNIPDAYAHPLF...YRGVDDSTGFRTRNILCFPIKNE.NQEVIGVAELVN.KINGP
CONSERVED      ---*---*---------------------L--P*------****----N-K----

CGB-PDE    A   GG...TFTEKDEKDFAAYLAFCGIVLHMAQL.YE
ROS-α      A   .....HFTENDEEILLKYLNFANLIMKVFHLSY.
ROS-β      A   .....CFTSEDEDVFLKYLNFGTLNLKIYHLSY.
CONE-α'    A   .....EFSKQDEEVFSKYLSFVSIILKLHHTNY.
CGS        A   .....LFTDQDEHVIQHCFHYTSTVL.TSTLAFQ
CGB-PDE    B   TGKVKAFNRNDEQFLEAFVIFCGLGIQNTQM.YE
ROS-α      B   .....FDEMDETLMESLAQFLGWSV.LNPDTYE
ROS-β      B   .....FVEQDEVLMESLTQFLGWSV.LNTDTYD
CONE-α'    B   .....FDEYDEHIAETLTQFLGWSL.LNTDTYE
CGS        B   .....WFSKFDEDLATAFSIYCGISI.AHSLLYK
CONSERVED      -----F----DE---------------*-----
```

FIGURE 3

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Arg Glu Xaa Asp Ala Asn Arg Ile Asn Tyr Met Tyr Ala Gln Tyr Val
 1               5                  10                  15
Lys Asn Thr Met
            20
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Gln  Ser  Leu  Ala  Ala  Ala  Val  Val  Pro
1                 5
```

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Phe  Asp  Asn  Asp  Glu  Gly  Glu  Gln
1                 5
```

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

```
TT Y GA Y AA Y G  A Y GARGGN-
GA   RCA                                                              23
```

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i v ) ANTI-SENSE: YES ( x i ) SEQUENCE DESCRIPTION: SEQ ID NO:5:

```
AARCTRTTRC  TRCT Y CCNCT   Y GT                                       23
```

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

```
AA Y TA Y ATGT  A Y GCNCAR-
TA   Y GT                                                             23
```

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i v ) ANTI-SENSE: YES ( x i ) SEQUENCE DESCRIPTION: SEQ ID NO:7:

```
TTRATRTACA TRCGNGT Y AT RCA                                              23
```

( 2 ) INFORMATION FOR SEQ ID NO:8:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( i v ) ANTI-SENSE: YES ( x i ) SEQUENCE DESCRIPTION: SEQ ID NO:8:

```
TTRATRTACA TRCGNGT Y AT RCANTT Y TTR TGNTAC                              36
```

( 2 ) INFORMATION FOR SEQ ID NO:9:

( i ) SEQUENCE CHARACTERISTICS:
        ( A ) LENGTH: 4474 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 99..2723

( x i ) SEQUENCE DESCRIPTION: SEQ ID NO:9:

```
GGGAGGGTCT CGAGGCGAGT TCTGCTCCTC GGAGGGAGGG ACCCCAGCTG GAGTGGAAAA                  60

CCAGCACCAG CTGACCGCAG AGACACGCCG CGCTGATC ATG GAG AGG GCC GGC                     113
                                          Met Glu Arg Ala Gly
                                            1               5

CCC GGC TCC GCG CGG CCG CAA CAG CAA TGG GAC CAG GAC TCG GTC GAA                   161
Pro Gly Ser Ala Arg Pro Gln Gln Gln Trp Asp Gln Asp Ser Val Glu
            10                  15                  20

GCG TGG CTG GAC GAT CAC TGG GAC TTT ACC TTC TCT TAC TTT GTT AGG                   209
Ala Trp Leu Asp Asp His Trp Asp Phe Thr Phe Ser Tyr Phe Val Arg
        25                  30                  35

AAA GGC ACC AGA GAA ATG GTC AAC GCA TGG TTT GCT GAG AGA GTT CAC                   257
Lys Gly Thr Arg Glu Met Val Asn Ala Trp Phe Ala Glu Arg Val His
    40                  45                  50

ACC ATT CCT GTG TGC AAG GAA GGA ATC AAG GGC CAC ACG GAA TCC TGC                   305
Thr Ile Pro Val Cys Lys Glu Gly Ile Lys Gly His Thr Glu Ser Cys
    55                  60                  65

TCT TGC CCC TTG CAG CCA AGT CCC CGT GCA GAG AGC AGT GTC CCT GGA                   353
Ser Cys Pro Leu Gln Pro Ser Pro Arg Ala Glu Ser Ser Val Pro Gly
70                  75                  80                  85

ACA CCA ACC AGG AAG ATC TCT GCC TCT GAA TTC GAT CGG CCG CTT AGA                   401
Thr Pro Thr Arg Lys Ile Ser Ala Ser Glu Phe Asp Arg Pro Leu Arg
```

```
              90                          95                          100
CCC ATC GTT ATC AAG GAT TCT GAG GGA ACT GTG AGC TTC CTC TCT GAC              449
Pro Ile Val Ile Lys Asp Ser Glu Gly Thr Val Ser Phe Leu Ser Asp
            105                         110                 115

TCA GAC AAG AAG GAA CAG ATG CCT CTA ACC TCC CCA CGG TTT GAT AAT              497
Ser Asp Lys Lys Glu Gln Met Pro Leu Thr Ser Pro Arg Phe Asp Asn
        120                         125                 130

GAT GAA GGG GAC CAG TGC TCG AGA CTC TTG GAA TTA GTG AAA GAT ATT              545
Asp Glu Gly Asp Gln Cys Ser Arg Leu Leu Glu Leu Val Lys Asp Ile
    135                         140                 145

TCT AGT CAC TTG GAT GTC ACA GCC TTA TGT CAC AAA ATT TTC TTG CAC              593
Ser Ser His Leu Asp Val Thr Ala Leu Cys His Lys Ile Phe Leu His
150                         155                 160                 165

ATC CAT GGA CTC ATC TCC GCC GAC CGC TAC TCC TTA TTC CTC GTC TGT              641
Ile His Gly Leu Ile Ser Ala Asp Arg Tyr Ser Leu Phe Leu Val Cys
                170                 175                 180

GAG GAC AGC TCC AAC GAC AAG TTT CTT ATC AGC CGC CTC TTT GAT GTT              689
Glu Asp Ser Ser Asn Asp Lys Phe Leu Ile Ser Arg Leu Phe Asp Val
            185                 190                 195

GCA GAA GGT TCA ACA CTG GAA GAA GCT TCA AAC AAC TGC ATC CGC TTA              737
Ala Glu Gly Ser Thr Leu Glu Glu Ala Ser Asn Asn Cys Ile Arg Leu
        200                 205                 210

GAG TGG AAC AAA GGC ATC GTG GGA CAC GTG GCC GCT TTT GGC GAG CCC              785
Glu Trp Asn Lys Gly Ile Val Gly His Val Ala Ala Phe Gly Glu Pro
    215                 220                 225

TTG AAC ATC AAA GAC GCC TAT GAG GAT CCT CGA TTC AAT GCA GAA GTT              833
Leu Asn Ile Lys Asp Ala Tyr Glu Asp Pro Arg Phe Asn Ala Glu Val
230                 235                 240                 245

GAC CAA ATT ACA GGC TAC AAG ACA CAA AGT ATT CTT TGT ATG CCA ATT              881
Asp Gln Ile Thr Gly Tyr Lys Thr Gln Ser Ile Leu Cys Met Pro Ile
                250                 255                 260

AAG AAT CAT AGG GAA GAG GTT GTT GGT GTA GCC CAG GCC ATC AAC AAG              929
Lys Asn His Arg Glu Glu Val Val Gly Val Ala Gln Ala Ile Asn Lys
            265                 270                 275

AAA TCA GGA AAT GGT GGG ACA TTC ACT GAA AAA GAC GAA AAG GAC TTT              977
Lys Ser Gly Asn Gly Gly Thr Phe Thr Glu Lys Asp Glu Lys Asp Phe
        280                 285                 290

GCT GCT TAC TTG GCA TTT TGT GGA ATT GTT CTT CAT AAT GCT CAA CTC             1025
Ala Ala Tyr Leu Ala Phe Cys Gly Ile Val Leu His Asn Ala Gln Leu
    295                 300                 305

TAT GAG ACT TCA CTG CTG GAG AAC AAG AGA AAT CAG GTG CTG CTT GAC             1073
Tyr Glu Thr Ser Leu Leu Glu Asn Lys Arg Asn Gln Val Leu Leu Asp
310                 315                 320                 325

CTT GCT AGC TTA ATT TTT GAA GAA CAA CAA TCA TTA GAA GTA ATT CTA             1121
Leu Ala Ser Leu Ile Phe Glu Glu Gln Gln Ser Leu Glu Val Ile Leu
                330                 335                 340

AAG AAA ATA GCT GCC ACT ATT ATC TCT TTC ATG CAG GTG CAG AAA TGC             1169
Lys Lys Ile Ala Ala Thr Ile Ile Ser Phe Met Gln Val Gln Lys Cys
            345                 350                 355

ACC ATT TTC ATA GTG GAT GAA GAT TGC TCC GAT TCT TTT TCT AGT GTG             1217
Thr Ile Phe Ile Val Asp Glu Asp Cys Ser Asp Ser Phe Ser Ser Val
        360                 365                 370

TTT CAC ATG GAG TGT GAG GAA TTA GAA AAA TCG TCA GAT ACT TTA ACA             1265
Phe His Met Glu Cys Glu Glu Leu Glu Lys Ser Ser Asp Thr Leu Thr
    375                 380                 385

CGG GAA CGT GAT GCA AAC AGA ATC AAT TAC ATG TAT GCT CAG TAT GTC             1313
Arg Glu Arg Asp Ala Asn Arg Ile Asn Tyr Met Tyr Ala Gln Tyr Val
390                 395                 400                 405

AAA AAT ACC ATG GAA CCA CTT AAT ATC CCA GAC GTC AGT AAG GAC AAA             1361
Lys Asn Thr Met Glu Pro Leu Asn Ile Pro Asp Val Ser Lys Asp Lys
```

```
                         410                          415                          420
AGA  TTT  CCC  TGG  ACA  AAT  GAA  AAC  ATG  GGA  AAT  ATA  AAC  CAG  CAG  TGC     1409
Arg  Phe  Pro  Trp  Thr  Asn  Glu  Asn  Met  Gly  Asn  Ile  Asn  Gln  Gln  Cys
               425                 430                 435

ATT  AGA  AGT  TTG  CTT  TGT  ACA  CCT  ATA  AAA  AAT  GGA  AAG  AAG  AAC  AAA     1457
Ile  Arg  Ser  Leu  Leu  Cys  Thr  Pro  Ile  Lys  Asn  Gly  Lys  Lys  Asn  Lys
               440                 445                 450

GTG  ATA  GGG  GTT  TGC  CAA  CTT  GTT  AAT  AAG  ATG  GAG  GAA  ACC  ACT  GGC     1505
Val  Ile  Gly  Val  Cys  Gln  Leu  Val  Asn  Lys  Met  Glu  Glu  Thr  Thr  Gly
               455                 460                 465

AAA  GTT  AAG  GCT  TTC  AAC  CGC  AAC  GAT  GAA  CAG  TTT  CTG  GAA  GCT  TTC     1553
Lys  Val  Lys  Ala  Phe  Asn  Arg  Asn  Asp  Glu  Gln  Phe  Leu  Glu  Ala  Phe
470                 475                 480                 485

GTC  ATC  TTT  TGT  GGC  TTG  GGG  ATC  CAG  AAC  ACA  CAG  ATG  TAC  GAA  GCA     1601
Val  Ile  Phe  Cys  Gly  Leu  Gly  Ile  Gln  Asn  Thr  Gln  Met  Tyr  Glu  Ala
                    490                 495                 500

GTG  GAG  AGA  GCC  ATG  GCC  AAG  CAA  ATG  GTC  ACG  TTA  GAG  GTT  CTG  TCT     1649
Val  Glu  Arg  Ala  Met  Ala  Lys  Gln  Met  Val  Thr  Leu  Glu  Val  Leu  Ser
               505                 510                 515

TAT  CAT  GCT  TCA  GCT  GCA  GAG  GAA  GAA  ACC  AGA  GAG  CTG  CAG  TCC  TTA     1697
Tyr  His  Ala  Ser  Ala  Ala  Glu  Glu  Glu  Thr  Arg  Glu  Leu  Gln  Ser  Leu
               520                 525                 530

GCG  GCT  GCT  GTG  GTA  CCA  TCT  GCC  CAG  ACC  CTT  AAA  ATC  ACT  GAC  TTC     1745
Ala  Ala  Ala  Val  Val  Pro  Ser  Ala  Gln  Thr  Leu  Lys  Ile  Thr  Asp  Phe
535                 540                 545

AGC  TTC  AGC  GAC  TTT  GAG  CTG  TCT  GAC  CTG  GAA  ACA  GCA  CTG  TGC  ACA     1793
Ser  Phe  Ser  Asp  Phe  Glu  Leu  Ser  Asp  Leu  Glu  Thr  Ala  Leu  Cys  Thr
550                 555                 560                 565

ATC  CGG  ATG  TTC  ACT  GAC  CTC  AAC  CTT  GTG  CAG  AAC  TTC  CAG  ATG  AAA     1841
Ile  Arg  Met  Phe  Thr  Asp  Leu  Asn  Leu  Val  Gln  Asn  Phe  Gln  Met  Lys
                    570                 575                 580

CAT  GAG  GTC  CTT  TGC  AAG  TGG  ATT  TTA  AGT  GTG  AAG  AAG  AAC  TAT  CGG     1889
His  Glu  Val  Leu  Cys  Lys  Trp  Ile  Leu  Ser  Val  Lys  Lys  Asn  Tyr  Arg
               585                 590                 595

AAG  AAC  GTC  GCC  TAT  CAT  AAT  TGG  AGA  CAT  GCC  TTT  AAT  ACA  GCT  CAG     1937
Lys  Asn  Val  Ala  Tyr  His  Asn  Trp  Arg  His  Ala  Phe  Asn  Thr  Ala  Gln
               600                 605                 610

TGC  ATG  TTT  GCG  GCA  CTA  AAA  GCA  GGC  AAA  ATT  CAG  AAG  AGG  CTG  ACG     1985
Cys  Met  Phe  Ala  Ala  Leu  Lys  Ala  Gly  Lys  Ile  Gln  Lys  Arg  Leu  Thr
               615                 620                 625

GAC  CTG  GAG  ATA  CTT  GCA  CTG  CTG  ATT  GCT  GCC  TTA  AGC  CAT  GAT  CTG     2033
Asp  Leu  Glu  Ile  Leu  Ala  Leu  Leu  Ile  Ala  Ala  Leu  Ser  His  Asp  Leu
630                 635                 640                 645

GAT  CAC  CGT  GGT  GTC  AAT  AAC  TCA  TAC  ATA  CAG  CGA  AGT  GAA  CAC  CCA     2081
Asp  His  Arg  Gly  Val  Asn  Asn  Ser  Tyr  Ile  Gln  Arg  Ser  Glu  His  Pro
                    650                 655                 660

CTT  GCT  CAG  CTC  TAC  TGC  CAT  TCA  ATC  ATG  GAG  CAT  CAT  CAT  TTT  GAT     2129
Leu  Ala  Gln  Leu  Tyr  Cys  His  Ser  Ile  Met  Glu  His  His  His  Phe  Asp
               665                 670                 675

CAG  TGC  CTG  ATG  ATC  CTT  AAT  AGT  CCT  GGC  AAT  CAG  ATT  CTC  AGT  GGC     2177
Gln  Cys  Leu  Met  Ile  Leu  Asn  Ser  Pro  Gly  Asn  Gln  Ile  Leu  Ser  Gly
               680                 685                 690

CTC  TCC  ATT  GAA  GAG  TAT  AAG  ACC  ACC  CTG  AAG  ATC  ATC  AAG  CAA  GCT     2225
Leu  Ser  Ile  Glu  Glu  Tyr  Lys  Thr  Thr  Leu  Lys  Ile  Ile  Lys  Gln  Ala
               695                 700                 705

ATT  TTA  GCC  ACA  GAC  CTA  GCA  CTG  TAC  ATA  AAG  AGA  CGA  GGA  GAA  TTT     2273
Ile  Leu  Ala  Thr  Asp  Leu  Ala  Leu  Tyr  Ile  Lys  Arg  Arg  Gly  Glu  Phe
710                 715                 720                 725

TTT  GAA  CTT  ATA  ATG  AAA  AAT  CAA  TTC  AAT  TTG  GAA  GAT  CCT  CAT  CAA     2321
Phe  Glu  Leu  Ile  Met  Lys  Asn  Gln  Phe  Asn  Leu  Glu  Asp  Pro  His  Gln
```

|   |   |   |   |   | 730 |   |   |   |   | 735 |   |   |   |   | 740 |   |   |
|---|---|---|---|---|---|---|---|---|---|---|---|---|---|---|---|---|---|

```
AAG GAG TTG TTT TTA GCG ATG CTG ATG ACA GCT TGT GAT CTT TCT GCA         2369
Lys Glu Leu Phe Leu Ala Met Leu Met Thr Ala Cys Asp Leu Ser Ala
            745             750                 755

ATT ACA AAA CCC TGG CCT ATT CAA CAA CGG ATA GCA GAA CTT GTT GCC         2417
Ile Thr Lys Pro Trp Pro Ile Gln Gln Arg Ile Ala Glu Leu Val Ala
            760             765                 770

ACT GAA TTT TTT GAC CAA GGA GAT AGA GAG AGG AAA GAA CTC AAC ATA         2465
Thr Glu Phe Phe Asp Gln Gly Asp Arg Glu Arg Lys Glu Leu Asn Ile
    775             780             785

GAG CCC GCT GAT CTA ATG AAC CGG GAG AAG AAA AAC AAA ATC CCA AGT         2513
Glu Pro Ala Asp Leu Met Asn Arg Glu Lys Lys Asn Lys Ile Pro Ser
790             795             800                 805

ATG CAA GTT GGA TTC ATA GAT GCC ATC TGC TTG CAA CTG TAT GAG GCC         2561
Met Gln Val Gly Phe Ile Asp Ala Ile Cys Leu Gln Leu Tyr Glu Ala
                810             815                 820

TTG ACC CAT GTG TCG GAG GAC TGT TTC CCT TTG CTG GAC GGC TGC AGA         2609
Leu Thr His Val Ser Glu Asp Cys Phe Pro Leu Leu Asp Gly Cys Arg
            825             830                 835

AAG AAC AGG CAG AAA TGG CAG GCT CTT GCA GAA CAG CAG GAG AAG ACA         2657
Lys Asn Arg Gln Lys Trp Gln Ala Leu Ala Glu Gln Gln Glu Lys Thr
            840             845                 850

CTG ATC AAT GGT GAA AGC AGC CAG ACC AAC CGA CAG CAA CGG AAT TCC         2705
Leu Ile Asn Gly Glu Ser Ser Gln Thr Asn Arg Gln Gln Arg Asn Ser
    855             860             865

GTT GCT GTC GGG ACA GTG TAGCCAGGTG TATCAGATGA GTGAGTGTGT                2753
Val Ala Val Gly Thr Val
870             875
```

```
GCTCAGCTCA GTCCTCTGCA ACACCATGAA GCTAGGCATT CCAGCTTAAT TCCTGCAGTT       2813
GACTTTAAAA AACTGGCATA AAGCACTAGT CAGCATCTAG TTCTAGCTTG ACCAGTGAAG       2873
AGTAGAACAC CACCACAGTC AGGGTGCAGA GCAGTTGGCA GTCTCCTTTC GAACCCAGAC       2933
TGGTGAATTT AAAGAAGAGC AGTCGTCGTT TATATCTCTG TCTTTTCCTA AGCGGGGTGT       2993
GGAATCTCTA AGAGGAGAGA GAGATCTGGA CCACAGGTCC AATGCGCTCT GTCCTCTCAG       3053
CTGCTTCCCC CACTGTGCTG TGACCTCTCA ATCTGAGAAA CGTGTAAGGA AGGTTTCAGC       3113
GAATTCCCTT TAAAATGTGT CAGACAGTAG CTTCTTGGGC CGGGTTGTTC CCGCAGCTCC       3173
CCATCTGTTT GTTGTCTATC TTGGCTGAAA GAGGCTTTGC TGTACCTGCC ACACTCTCCT       3233
GGATCCCTGT CCAGTAGCTG ATCAAAAAAA AGGATGTGAA ATTCTCGTGT GACTTTTTAG       3293
AAAAGGAAAG TGACCCCGAG GATCGGTGTG GATTCACTAG TTGTCCACAG ATGATCTGTT       3353
TAGTTTCTAG AATTTTCCAA GATGATACAC TCCTCCCTAG TCTAGGGGTC AGACCCTGTA       3413
TGGTGGCTGT GACCCTTGAG GAACTTCTCT CTTTGCATGA CATTAGCCAT GAACTGTTC        3473
TTGTCCAAAT ACACAGCTCA TATGCAGCTT GCAGGAAACA CTTTAAAAAC ACAACTATCA       3533
CCTATGTTAT TCTGATTACA GAAGTTATCC CTACTCACTG TAAACATAAA CAAAGCCCCC       3593
CAAACTTCAA ATAGTTGTGT GTGGTGAGAA ACTGCAAGTT TTCATCTCCA GAGATAGCTA       3653
TAGGTAATAA GTGGGATGTT TCTGAAACTT TTAAAAATAA TCTTTTACAT ATATGTTAAC       3713
TGTTTTCTTA TGAGCACTAT GGTTTGTTTT TTTTTTTTT TGCTCTGCTT TGACTTGCCC        3773
TTTTCACTCA ATTATCTTGG CAGTTTTTCT AAATGACTTG CACAGACTTC TCCTGTACTT       3833
CATGGCTGTG CAGTGTTCCA TGCTGTGAGG GCACCATCGT GTATTAAATC AGTTCCCTGG       3893
TCACACATAG GTGAGCTGGT TGGAAATTTT TACCATTAAA AAACCACTTT CCCACATTGA       3953
TGCTTTCTAA TCTGGCACAG GATGCTTCTT TTTTTCCCCT TTTTCTCTGT TTAATTATTG       4013
```

-continued

```
GAAATGGGAT CTGTGGGATC CTCGTTCCCT GGCACCTAGC TGCTCTCAAC GTGGCCTGTG      4073

GCCAGCAGCA TTGGCTAGAC CTGGGGGCTT GTTGGGAACG GAGACCCTCT GCCCTGCCCC      4133

TGGCCTGCTG ACAAGGACCT GCATTTTGCT GAGCTCCCAG TGACCCTGGT GTTTAATTGT      4193

TAACCATTGA AAAAAATCAA ACTATAGTTT ATTTACAATG TTGTGTTAAT TTCGGGTGTA      4253

CAGCAAAGTG ACTCAGTGGT CAAGTACATT TAAAACACTG GCATACTCT CTCCCTCTCC       4313

TTGTGTACCT GGTTGGTATT TCCAGAAACC ATGCTCTTGT CTGTCCTGTA GTTTGGAAG       4373

CGCTTTCTCT TTGAAGACTG CCTTCTCTCC TCTGTCTGCC CTACATGGAC TAGTTCGTTT      4433

ATTGTCCTAC ATGGCTTTGC TTCCATGTTC CTCTCAACTT T                          4474
```

( 2 ) INFORMATION FOR SEQ ID NO:10:

( i ) SEQUENCE CHARACTERISTICS:
        ( A ) LENGTH: 875 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Glu Arg Ala Gly Pro Gly Ser Ala Arg Pro Gln Gln Gln Trp Asp
 1               5                  10                  15

Gln Asp Ser Val Glu Ala Trp Leu Asp Asp His Trp Asp Phe Thr Phe
            20                  25                  30

Ser Tyr Phe Val Arg Lys Gly Thr Arg Glu Met Val Asn Ala Trp Phe
        35                  40                  45

Ala Glu Arg Val His Thr Ile Pro Val Cys Lys Glu Gly Ile Lys Gly
    50                  55                  60

His Thr Glu Ser Cys Ser Cys Pro Leu Gln Pro Ser Pro Arg Ala Glu
65                  70                  75                  80

Ser Ser Val Pro Gly Thr Pro Thr Arg Lys Ile Ser Ala Ser Glu Phe
                85                  90                  95

Asp Arg Pro Leu Arg Pro Ile Val Ile Lys Asp Ser Glu Gly Thr Val
            100                 105                 110

Ser Phe Leu Ser Asp Ser Asp Lys Lys Glu Gln Met Pro Leu Thr Ser
        115                 120                 125

Pro Arg Phe Asp Asn Asp Glu Gly Asp Gln Cys Ser Arg Leu Leu Glu
    130                 135                 140

Leu Val Lys Asp Ile Ser Ser His Leu Asp Val Thr Ala Leu Cys His
145                 150                 155                 160

Lys Ile Phe Leu His Ile His Gly Leu Ile Ser Ala Asp Arg Tyr Ser
                165                 170                 175

Leu Phe Leu Val Cys Glu Asp Ser Ser Asn Asp Lys Phe Leu Ile Ser
            180                 185                 190

Arg Leu Phe Asp Val Ala Glu Gly Ser Thr Leu Glu Glu Ala Ser Asn
        195                 200                 205

Asn Cys Ile Arg Leu Glu Trp Asn Lys Gly Ile Val Gly His Val Ala
    210                 215                 220

Ala Phe Gly Glu Pro Leu Asn Ile Lys Asp Ala Tyr Glu Asp Pro Arg
225                 230                 235                 240

Phe Asn Ala Glu Val Asp Gln Ile Thr Gly Tyr Lys Thr Gln Ser Ile
                245                 250                 255

Leu Cys Met Pro Ile Lys Asn His Arg Glu Glu Val Val Gly Val Ala
            260                 265                 270

Gln Ala Ile Asn Lys Lys Ser Gly Asn Gly Gly Thr Phe Thr Glu Lys
```

|   |   |   | 275 |   |   |   | 280 |   |   |   | 285 |   |   |   |
|---|---|---|---|---|---|---|---|---|---|---|---|---|---|---|
| Asp | Glu | Lys | Asp | Phe | Ala | Ala | Tyr | Leu | Ala | Phe | Cys | Gly | Ile | Val | Leu |
|   | 290 |   |   |   | 295 |   |   |   | 300 |   |   |   |   |   |
| His | Asn | Ala | Gln | Leu | Tyr | Glu | Thr | Ser | Leu | Leu | Glu | Asn | Lys | Arg | Asn |
| 305 |   |   |   |   | 310 |   |   |   | 315 |   |   |   |   |   | 320 |
| Gln | Val | Leu | Leu | Asp | Leu | Ala | Ser | Leu | Ile | Phe | Glu | Glu | Gln | Ser |
|   |   |   |   | 325 |   |   |   | 330 |   |   |   |   | 335 |   |
| Leu | Glu | Val | Ile | Leu | Lys | Lys | Ile | Ala | Ala | Thr | Ile | Ile | Ser | Phe | Met |
|   |   |   | 340 |   |   |   | 345 |   |   |   |   |   | 350 |   |   |
| Gln | Val | Gln | Lys | Cys | Thr | Ile | Phe | Ile | Val | Asp | Glu | Asp | Cys | Ser | Asp |
|   |   | 355 |   |   |   |   | 360 |   |   |   |   | 365 |   |   |   |
| Ser | Phe | Ser | Ser | Val | Phe | His | Met | Glu | Cys | Glu | Glu | Leu | Glu | Lys | Ser |
|   | 370 |   |   |   |   |   | 375 |   |   |   |   | 380 |   |   |   |
| Ser | Asp | Thr | Leu | Thr | Arg | Glu | Arg | Asp | Ala | Asn | Arg | Ile | Asn | Tyr | Met |
| 385 |   |   |   |   | 390 |   |   |   | 395 |   |   |   |   |   | 400 |
| Tyr | Ala | Gln | Tyr | Val | Lys | Asn | Thr | Met | Glu | Pro | Leu | Asn | Ile | Pro | Asp |
|   |   |   |   | 405 |   |   |   | 410 |   |   |   |   | 415 |   |   |
| Val | Ser | Lys | Asp | Lys | Arg | Phe | Pro | Trp | Thr | Asn | Glu | Asn | Met | Gly | Asn |
|   |   |   | 420 |   |   |   |   | 425 |   |   |   |   | 430 |   |   |
| Ile | Asn | Gln | Gln | Cys | Ile | Arg | Ser | Leu | Leu | Cys | Thr | Pro | Ile | Lys | Asn |
|   |   | 435 |   |   |   |   | 440 |   |   |   |   | 445 |   |   |   |
| Gly | Lys | Lys | Asn | Lys | Val | Ile | Gly | Val | Cys | Gln | Leu | Val | Asn | Lys | Met |
|   | 450 |   |   |   |   | 455 |   |   |   |   | 460 |   |   |   |   |
| Glu | Glu | Thr | Thr | Gly | Lys | Val | Lys | Ala | Phe | Asn | Arg | Asn | Asp | Glu | Gln |
| 465 |   |   |   |   | 470 |   |   |   |   | 475 |   |   |   |   | 480 |
| Phe | Leu | Glu | Ala | Phe | Val | Ile | Phe | Cys | Gly | Leu | Gly | Ile | Gln | Asn | Thr |
|   |   |   |   | 485 |   |   |   | 490 |   |   |   |   | 495 |   |   |
| Gln | Met | Tyr | Glu | Ala | Val | Glu | Arg | Ala | Met | Ala | Lys | Gln | Met | Val | Thr |
|   |   |   | 500 |   |   |   | 505 |   |   |   |   | 510 |   |   |   |
| Leu | Glu | Val | Leu | Ser | Tyr | His | Ala | Ser | Ala | Ala | Glu | Glu | Glu | Thr | Arg |
|   |   | 515 |   |   |   |   | 520 |   |   |   |   | 525 |   |   |   |
| Glu | Leu | Gln | Ser | Leu | Ala | Ala | Ala | Val | Val | Pro | Ser | Ala | Gln | Thr | Leu |
|   | 530 |   |   |   |   | 535 |   |   |   |   | 540 |   |   |   |   |
| Lys | Ile | Thr | Asp | Phe | Ser | Phe | Ser | Asp | Phe | Glu | Leu | Ser | Asp | Leu | Glu |
| 545 |   |   |   |   | 550 |   |   |   | 555 |   |   |   |   |   | 560 |
| Thr | Ala | Leu | Cys | Thr | Ile | Arg | Met | Phe | Thr | Asp | Leu | Asn | Leu | Val | Gln |
|   |   |   |   | 565 |   |   |   | 570 |   |   |   |   | 575 |   |   |
| Asn | Phe | Gln | Met | Lys | His | Glu | Val | Leu | Cys | Lys | Trp | Ile | Leu | Ser | Val |
|   |   |   | 580 |   |   |   | 585 |   |   |   |   | 590 |   |   |   |
| Lys | Lys | Asn | Tyr | Arg | Lys | Asn | Val | Ala | Tyr | His | Asn | Trp | Arg | His | Ala |
|   |   | 595 |   |   |   |   | 600 |   |   |   |   | 605 |   |   |   |
| Phe | Asn | Thr | Ala | Gln | Cys | Met | Phe | Ala | Ala | Leu | Lys | Ala | Gly | Lys | Ile |
|   | 610 |   |   |   |   | 615 |   |   |   |   | 620 |   |   |   |   |
| Gln | Lys | Arg | Leu | Thr | Asp | Leu | Glu | Ile | Leu | Ala | Leu | Leu | Ile | Ala | Ala |
| 625 |   |   |   |   | 630 |   |   |   | 635 |   |   |   |   |   | 640 |
| Leu | Ser | His | Asp | Leu | Asp | His | Arg | Gly | Val | Asn | Asn | Ser | Tyr | Ile | Gln |
|   |   |   |   | 645 |   |   |   | 650 |   |   |   |   | 655 |   |   |
| Arg | Ser | Glu | His | Pro | Leu | Ala | Gln | Leu | Tyr | Cys | His | Ser | Ile | Met | Glu |
|   |   |   | 660 |   |   |   | 665 |   |   |   |   | 670 |   |   |   |
| His | His | His | Phe | Asp | Gln | Cys | Leu | Met | Ile | Leu | Asn | Ser | Pro | Gly | Asn |
|   |   | 675 |   |   |   |   | 680 |   |   |   |   | 685 |   |   |   |
| Gln | Ile | Leu | Ser | Gly | Leu | Ser | Ile | Glu | Glu | Tyr | Lys | Thr | Thr | Leu | Lys |
|   | 690 |   |   |   |   | 695 |   |   |   |   | 700 |   |   |   |   |

| | | | | | | | | | | | | | | |
|---|---|---|---|---|---|---|---|---|---|---|---|---|---|---|
| Ile | Ile | Lys | Gln | Ala | Ile | Leu | Ala | Thr | Asp | Leu | Ala | Leu | Tyr | Ile | Lys |
| 705 | | | | | 710 | | | | 715 | | | | | 720 |

Arg Arg Gly Glu Phe Phe Glu Leu Ile Met Lys Asn Gln Phe Asn Leu
            725                 730                 735

Glu Asp Pro His Gln Lys Glu Leu Phe Leu Ala Met Leu Met Thr Ala
            740                 745                 750

Cys Asp Leu Ser Ala Ile Thr Lys Pro Trp Pro Ile Gln Gln Arg Ile
            755                 760                 765

Ala Glu Leu Val Ala Thr Glu Phe Phe Asp Gln Gly Asp Arg Glu Arg
            770                 775                 780

Lys Glu Leu Asn Ile Glu Pro Ala Asp Leu Met Asn Arg Glu Lys Lys
785                 790                 795                 800

Asn Lys Ile Pro Ser Met Gln Val Gly Phe Ile Asp Ala Ile Cys Leu
            805                 810                 815

Gln Leu Tyr Glu Ala Leu Thr His Val Ser Glu Asp Cys Phe Pro Leu
            820                 825                 830

Leu Asp Gly Cys Arg Lys Asn Arg Gln Lys Trp Gln Ala Leu Ala Glu
            835                 840                 845

Gln Gln Glu Lys Thr Leu Ile Asn Gly Glu Ser Ser Gln Thr Asn Arg
850                 855                 860

Gln Gln Arg Asn Ser Val Ala Val Gly Thr Val
865             870             875

( 2 ) INFORMATION FOR SEQ ID NO:11:

( i ) SEQUENCE CHARACTERISTICS:
        ( A ) LENGTH: 2060 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
GCGGCCGCGC TCCGGCCGCT TTGTCGAAAG CCGGCCCGAC TGGAGCAGGA CGAAGGGGGA        60
GGGTCTCGAG GCCGAGTCCT GTTCTTCTGA GGGACGGACC CCAGCTGGGG TGGAAAAGCA       120
GTACCAGAGA GCCTCCGAGG CGCGCGGTGC CAACCATGGA GCGGGCCGGC CCCAGCTTCG       180
GGCAGCAGCG ACAGCAGCAG CAGCCCCAGC AGCAGAAGCA GCAGCAGAGG GATCAGGACT       240
CGGTCGAAGC ATGGCTGGAC GATCACTGGG ACTTTACCTT CTCATACTTT GTTAGAAAAG       300
CCACCAGAGA AATGGTCAAT GCATGGTTTG CTGAGAGAGT TCACACCATC CCTGTGTGCA       360
AGGAAGGTAT CAGAGGCCAC ACCGAATCTT GCTCTTGTCC CTTGCAGCAG AGTCCTCGTG       420
CAGATAACAG TGTCCCTGGA ACACCAACCA GGAAAATCTC TGCCTCTGAA TTTGACCGGC       480
CTCTTAGACC CATTGTTGTC AAGGATTCTG AGGGAACTGT GAGCTTCCTC TCTGACTCAG       540
AAAAGAAGGA ACAGATGCCT CTAACCCCTC AAGGTTTGA TCATGATGAA GGGGACCAGT       600
GCTCAAGACT CTTGGAATTA GTGAAGGATA TTTCTAGTCA TTTGGATGTC ACAGCCTTAT       660
GTCACAAAAT TTTCTTGCAT ATCCATGGAC TGATATCTGC TGACCGCTAT TCCCTGTTCC       720
TTGTCTGTGA AGACAGCTCC AATGACAAGT TTCTTATCAG CCGCCTCTTT GATGTTGCTG       780
AAGGTTCAAC ACTGGAAGAA GTTTCAAATA ACTGTATCCG CTTAGAATGG AACAAAGGCA       840
TTGTGGGACA TGTGGCAGCG CTTGGTGAGC CCTTGAACAT CAAAGATGCA TATGAGGATC       900
CTCGGTTCAA TGCAGAAGTT GACCAAATTA CAGGCTACAA GACACAAAGC ATTCTTTGTA       960
TGCCAATTAA GAATCATAGG GAAGAGGTTG TTGGTGTAGC CCAGGCCATC AACAAGAAAT      1020
```

```
CAGGAAACGG TGGGACATTT ACTGAAAAAG ATGAAAAGGA CTTTGCTGCT TATTTGGCAT    1080
TTTGTGGTAT TGTTCTTCAT AATGCTCAGC TCTATGAGAC TTCACTGCTG GAGAACAAGA    1140
GAAATCAGGT GCTGCTTGAC CTTGCTAGTT TAATTTTTGA AGAACAACAA TCATTAGAAG    1200
TAATTTTGAA GAAAATAGCT GCCACTATTA TCTCTTTCAT GCAAGTGCAG AAATGCACCA    1260
TTTTCATAGT GGATGAAGAT TGCTCCGATT CTTTTCTAG  TGTGTTTCAC ATGGAGTGTG    1320
AGGAATTAGA AAAATCATCT GATACATTAA CAAGGGAACA TGATGCAAAC AAAATCAATT    1380
ACATGTATGC TCAGTATGTC AAAAATACTA TGGAACCACT TTATATCCCA GATGTCAGTA    1440
AGGATAAAAG ATTTCCCTGG ACAACTGAAA ATACAGGAAA TGTAAACCAG CAGTGCATTA    1500
GAAGTTTGCT TTGTACACCT ATAAAAATG  GAAGAAGAA  TAAAGTTATA GGGGTTTGCC    1560
AACTTGTTAA TAAGATGGAG GAGAATACTG GCAAGGTTAA GCCTTTCAAC CGAAATGACG    1620
AACAGTTTCT GGAAGCTTTT GTCATCTTTT GTGGCTTGGG GATCCAGAAC ACGCAGATGT    1680
ATGAAGCAGT GGAGAGAGCC ATGGCCAAGC AAATGGTCAC ATTGGAGGTT CTGTCGTATC    1740
ATGCTTCAGC AGCAGAGGAA GAAACAAGAG AGCTACAGTC GTTAGCGGCT GCTGTGGTGC    1800
CATCTGCCCA GACCCTTAAA ATTACTGACT TTAGCTTCAG TGACTTTGAG CTGTCTGATC    1860
TGGAAACAGC ACTGTGTACA ATTCGGATGT TTACTGACCT CAACCTTGTG CAGAACTTCC    1920
AGATGAAACA TGAGGTTCTT TGCAGATGGA TTTTAAGTGT TAAGAAGAAT TATCGGAAGA    1980
ATGTTGCCTA TCATAATTGG AGACATGCCT TTAATACAGC TCAGTGCATG TTTGCTGCTC    2040
TAAAAGCAGG CAAAATTCAG                                                2060
```

( 2 ) INFORMATION FOR SEQ ID NO:12:

( i ) SEQUENCE CHARACTERISTICS:
        ( A ) LENGTH: 1982 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

```
ACAAAATTTT CTTGCATATC CATGGACTGA TATCTGCTGA CCGCTATTCC CTGTTCCTTG     60
TCTGTGAAGA CAGCTCCAAT GACAAGTTTC TTATCAGCCG CCTCTTTGAT GTTGCTGAAG    120
GTTCAACACT GGAAGAAGTT TCAAATAACT GTATCCGCTT AGAATGGAAC AAAGGCATTG    180
TGGGACATGT GGCAGCGCTT GGTGAGCCCT TGAACATCAA AGATGCATAT GAGGATCCTC    240
GGTTCAATGC AGAAGTTGAC CAAATTACAG GCTACAAGAC ACAAAGCATT CTTTGTATGC    300
CAATTAAGAA TCATAGGGAA GAGGTTGTTG GTGTAGCCCA GGCCATCAAC AAGAAATCAG    360
GAAACGGTGG ACATTTACT  GAAAAGATG  AAAAGGACTT TGCTGCTTAT TTGGCATTTT    420
GTGGTATTGT TCTTCATAAT GCTCAGCTCT ATGAGACTTC ACTGCTGGAG AACAAGAGAA    480
ATCAGGTGCT GCTTGACCTT GCTAGTTTAA TTTTTGAAGA ACAACAATCA TTAGAAGTAA    540
TTTTGAAGAA AATAGCTGCC ACTATTATCT CTTCATGCA  AGTGCAGAAA TGCACCATTT    600
TCATAGTGGA TGAAGATTGC TCCGATTCTT TTCTAGTGT  GTTCACATG  GAGTGTGAGG    660
AATTAGAAAA ATCATCTGAT ACATTAACAA GGGAACATGA TGCAAACAAA TCAATTACA     720
TGTATGCTCA GTATGTCAAA AATACTATGG AACCACTTAA TATCCCAGAT GTCAGTAAGG    780
ATAAAAGATT TCCCTGGACA ACTGAAAATA CAGGAAATGT AAACCAGCAG TGCATTAGAA    840
GTTTGCTTTG TACACCTATA AAAATGGAA  AGAAGAATAA AGTTATAGGG TTTGCCAAC     900
TTGTTAATAA GATGGAGGAG AATACTGGCA AGGTTAAGCC TTTCAACCGA AATGACGAAC    960
```

| | | | | | | |
|---|---|---|---|---|---|---|
| AGTTTCTGGA | AGCTTTTGTC | ATCTTTTGTG | GCTTGGGGAT | CCAGAACACG | CAGATGTATG | 1020 |
| AAGCAGTGGA | GAGAGCCATG | GCCAAGCAAA | TGGTCACATT | GGAGGTTCTG | TCGTATCATG | 1080 |
| CTTCAGCAGC | AGAGGAAGAA | ACAAGAGAGC | TACAGTCGTT | AGCGGCTGCT | GTGGTGCCAT | 1140 |
| CTGCCCAGAC | CCTTAAAATT | ACTGACTTTA | GCTTCAGTGA | CTTTGAGCTG | TCTGATCTGG | 1200 |
| AAACAGCACT | GTGTACAATT | CGGATGTTTA | CTGACCTCAA | CCTTGTGCAG | AACTTCCAGA | 1260 |
| TGAAACATGA | GGTTCTTTGC | AGATGGATTT | TAAGTGTTAA | GAAGAATTAT | CGGAAGAATG | 1320 |
| TTGCCTATCA | TAATTGGAGA | CATGCCTTTA | ATACAGCTCA | GTGCATGTTT | GCTGCTCTAA | 1380 |
| AAGCAGGCAA | AATTCAGAAC | AAGCTGACTG | ACCTGGAGAT | ACTTGCATTG | CTGATTGCTG | 1440 |
| CACTAAGCCA | CGATTGGAT | CACCGTGGTG | TGAATAACTC | TTACATACAG | CGAAGTGAAC | 1500 |
| ATCCACTTGC | CCAGCTTTAC | TGCCATTCAA | TCATGGAACA | CCATCATTTT | GACCAGTGCC | 1560 |
| TGATGATTCT | TAATAGTCCA | GGCAATCAGA | TTCTCAGTGG | CCTCTCCATT | GAAGAATATA | 1620 |
| AGACCACGTT | GAAAATAATC | AAGCAAGCTA | TTTTAGCTAC | AGACCTAGCA | CTGTACATTA | 1680 |
| AGAGGCGAGG | AGAATTTTTT | GAACTTATAA | GAAAAAATCA | ATTCAATTTG | GAAGATCCTC | 1740 |
| ATCAAAGGA | GTTGTTTTG | GCAATGCTGA | TGACAGCTTG | TGATCTTTCT | GCAATTACAA | 1800 |
| AACCCTGGCC | TATTCAACAA | CGGATAGCAG | AACTTGTAGC | AACTGAATTT | TTTGATCAAG | 1860 |
| GAGACAGAGA | GAGAAAAGAA | CTCAACATAG | AACCCACTGA | TCTAATGAAC | AGGGAGAAGA | 1920 |
| AAAACAAAAT | CCCAAGTATG | CAAGTTGGGT | TCATAGATGC | CATCTGCTTG | CAACTGTATG | 1980 |
| AG | | | | | | 1982 |

(2) INFORMATION FOR SEQ ID NO:13:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:13:

GCCACCAGAG AAATGGTC     18

(2) INFORMATION FOR SEQ ID NO:14:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:14:

ACAATGGGTC TAAGAGGC     18

(2) INFORMATION FOR SEQ ID NO:15:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:15:

```
TCAGTGCATG TTTGCTGC                                                                                          18
```

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

```
TACAAACATG TTCATCAG                                                                                          18
```

( 2 ) INFORMATION FOR SEQ ID NO:17:

( i ) SEQUENCE CHARACTERISTICS:
        ( A ) LENGTH: 1107 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

```
GAGACATGCC  TTTAATACAG  CTCAGTGCAT  GTTTGCTGCT  CTAAAAGCAG  GCAAAATTCA    60
GAACAAGCTG  ACTGACCTGG  AGATACTTGC  ATTGCTGATT  GCTGCACTAA  GCCACGATTT   120
GGATCACCGT  GGTGTGAATA  ACTCTTACAT  ACAGCGAAGT  GAACATCCAC  TTGCCCAGCT   180
TTACTGCCAT  TCAATCATGG  AACACCATCA  TTTTGACCAG  TGCCTGATGA  TTCTTAATAG   240
TCCAGGCAAT  CAGATTCTCA  GTGGCCTCTC  CATTGAAGAA  TATAAGACCA  CGTTGAAAAT   300
AATCAAGCAA  GCTATTTTAG  CTACAGACCT  AGCACTGTAC  ATTAAGAGGC  GAGGAGAATT   360
TTTTGAACTT  ATAAGAAAAA  ATCAATTCAA  TTTGGAAGAT  CCTCATCAAA  AGGAGTTGTT   420
TTTGGCAATG  CTGATGACAG  CTTGTGATCT  TTCTGCAATT  ACAAAACCCT  GGCCTATTCA   480
ACAACGGATA  GCAGAACTTG  TAGCAACTGA  ATTTTTTGAT  CAAGGAGACA  GAGAGAGAAA   540
AGAACTCAAC  ATAGAACCCA  CTGATCTAAT  GAACAGGGAG  AAGAAAAACA  AATCCCAAG    600
TATGCAAGTT  GGGTTCATAG  ATGCCATCTG  CTTGCAACTG  TATGAGGCCC  TGACCCACGT   660
GTCAGAGGAC  TGTTTCCCTT  TGCTAGATGG  CTGCAGAAAG  AACAGGCAGA  ATGGCAGGC    720
CCTTGCAGAA  CAGCAGGAGA  AGATGCTGAT  TAATGGGGAA  AGCGGCCAGG  CCAAGCGGAA   780
CTGAGTGGCC  TATTTCATGC  AGAGTTGAAG  TTTACAGAGA  TGGTGTGTTC  TGCAATATGC   840
CTAGTTTCTT  ACACACTGTC  TGTATAGTGT  CTGTATTTGG  TATATACTTT  GCCACTGCTG   900
TATTTTTATT  TTTGCACAAC  TTTTGAGAGT  ATAGCATGAA  TGTTTTTAGA  GGACTATTAC   960
ATATTTTTTG  TATATTTGTT  TTATGCTACT  GAACTGAAAG  GATCAACAAC  ATCCACTGTT  1020
AGCACATTGA  TAAAAGCATT  GTTTGTGATA  TTTCGTGTAC  TGCAAAGTGT  ATGCAGTATT  1080
CTTGCACTGA  GGTTTTTTTG  CTTGGGG                                         1107
```

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

```
TTTGGAAGAT CCTCATCA                                                               18
```

( 2 ) INFORMATION FOR SEQ ID NO:19:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

```
ATGTCTCGAG TCAGTTCCGC TTGGCCTG                                                    28
```

( 2 ) INFORMATION FOR SEQ ID NO:20:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

```
TACAGAATTC TGACCATGGA GCGGGCCGGC                                                  30
```

( 2 ) INFORMATION FOR SEQ ID NO:21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

```
CATTCTAAGC GGATACAG                                                               18
```

( 2 ) INFORMATION FOR SEQ ID NO:22:

( i ) SEQUENCE CHARACTERISTICS:
        ( A ) LENGTH: 2645 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 12..2636

( x i ) SEQUENCE DESCRIPTION: SEQ ID NO:22:

```
GAATTCTGAC C ATG GAG CGG GCC GGC CCC AGC TTC GGG CAG CAG CGA CAG         50
            Met Glu Arg Ala Gly Pro Ser Phe Gly Gln Gln Arg Gln
             1               5                  10

CAG CAG CAG CCC CAG CAG CAG AAG CAG CAG CAG AGG GAT CAG GAC TCG         98
Gln Gln Gln Pro Gln Gln Gln Lys Gln Gln Gln Arg Asp Gln Asp Ser
         15                  20                  25

GTC GAA GCA TGG CTG GAC GAT CAC TGG GAC TTT ACC TTC TCA TAC TTT        146
Val Glu Ala Trp Leu Asp Asp His Trp Asp Phe Thr Phe Ser Tyr Phe
 30                  35                  40                  45

GTT AGA AAA GCC ACC AGA GAA ATG GTC AAT GCA TGG TTT GCT GAG AGA        194
Val Arg Lys Ala Thr Arg Glu Met Val Asn Ala Trp Phe Ala Glu Arg
```

-continued

|  |  |  | 50 |  |  |  | 55 |  |  |  | 60 |  |  |  |
|---|---|---|---|---|---|---|---|---|---|---|---|---|---|---|

```
GTT  CAC  ACC  ATC  CCT  GTG  TGC  AAG  GAA  GGT  ATC  AGA  GGC  CAC  ACC  GAA      242
Val  His  Thr  Ile  Pro  Val  Cys  Lys  Glu  Gly  Ile  Arg  Gly  His  Thr  Glu
               65                      70                      75

TCT  TGC  TCT  TGT  CCC  TTG  CAG  CAG  AGT  CCT  CGT  GCA  GAT  AAC  AGT  GTC      290
Ser  Cys  Ser  Cys  Pro  Leu  Gln  Gln  Ser  Pro  Arg  Ala  Asp  Asn  Ser  Val
               80                      85                      90

CCT  GGA  ACA  CCA  ACC  AGG  AAA  ATC  TCT  GCC  TCT  GAA  TTT  GAC  CGG  CCT      338
Pro  Gly  Thr  Pro  Thr  Arg  Lys  Ile  Ser  Ala  Ser  Glu  Phe  Asp  Arg  Pro
     95                      100                     105

CTT  AGA  CCC  ATT  GTT  GTC  AAG  GAT  TCT  GAG  GGA  ACT  GTG  AGC  TTC  CTC      386
Leu  Arg  Pro  Ile  Val  Val  Lys  Asp  Ser  Glu  Gly  Thr  Val  Ser  Phe  Leu
110                      115                     120                     125

TCT  GAC  TCA  GAA  AAG  AAG  GAA  CAG  ATG  CCT  CTA  ACC  CCT  CCA  AGG  TTT      434
Ser  Asp  Ser  Glu  Lys  Lys  Glu  Gln  Met  Pro  Leu  Thr  Pro  Pro  Arg  Phe
               130                     135                     140

GAT  CAT  GAT  GAA  GGG  GAC  CAG  TGC  TCA  AGA  CTC  TTG  GAA  TTA  GTG  AAG      482
Asp  His  Asp  Glu  Gly  Asp  Gln  Cys  Ser  Arg  Leu  Leu  Glu  Leu  Val  Lys
               145                     150                     155

GAT  ATT  TCT  AGT  CAT  TTG  GAT  GTC  ACA  GCC  TTA  TGT  CAC  AAA  ATT  TTC      530
Asp  Ile  Ser  Ser  His  Leu  Asp  Val  Thr  Ala  Leu  Cys  His  Lys  Ile  Phe
               160                     165                     170

TTG  CAT  ATC  CAT  GGA  CTG  ATA  TCT  GCT  GAC  CGC  TAT  TCC  CTG  TTC  CTT      578
Leu  His  Ile  His  Gly  Leu  Ile  Ser  Ala  Asp  Arg  Tyr  Ser  Leu  Phe  Leu
175                      180                     185

GTC  TGT  GAA  GAC  AGC  TCC  AAT  GAC  AAG  TTT  CTT  ATC  AGC  CGC  CTC  TTT      626
Val  Cys  Glu  Asp  Ser  Ser  Asn  Asp  Lys  Phe  Leu  Ile  Ser  Arg  Leu  Phe
190                      195                     200                     205

GAT  GTT  GCT  GAA  GGT  TCA  ACA  CTG  GAA  GAA  GTT  TCA  AAT  AAC  TGT  ATC      674
Asp  Val  Ala  Glu  Gly  Ser  Thr  Leu  Glu  Glu  Val  Ser  Asn  Asn  Cys  Ile
               210                     215                     220

CGC  TTA  GAA  TGG  AAC  AAA  GGC  ATT  GTG  GGA  CAT  GTG  GCA  GCG  CTT  GGT      722
Arg  Leu  Glu  Trp  Asn  Lys  Gly  Ile  Val  Gly  His  Val  Ala  Ala  Leu  Gly
               225                     230                     235

GAG  CCC  TTG  AAC  ATC  AAA  GAT  GCA  TAT  GAG  GAT  CCT  CGG  TTC  AAT  GCA      770
Glu  Pro  Leu  Asn  Ile  Lys  Asp  Ala  Tyr  Glu  Asp  Pro  Arg  Phe  Asn  Ala
          240                     245                     250

GAA  GTT  GAC  CAA  ATT  ACA  GGC  TAC  AAG  ACA  CAA  AGC  ATT  CTT  TGT  ATG      818
Glu  Val  Asp  Gln  Ile  Thr  Gly  Tyr  Lys  Thr  Gln  Ser  Ile  Leu  Cys  Met
255                      260                     265

CCA  ATT  AAG  AAT  CAT  AGG  GAA  GAG  GTT  GTT  GGT  GTA  GCC  CAG  GCC  ATC      866
Pro  Ile  Lys  Asn  His  Arg  Glu  Glu  Val  Val  Gly  Val  Ala  Gln  Ala  Ile
270                      275                     280                     285

AAC  AAG  AAA  TCA  GGA  AAC  GGT  GGG  ACA  TTT  ACT  GAA  AAA  GAT  GAA  AAG      914
Asn  Lys  Lys  Ser  Gly  Asn  Gly  Gly  Thr  Phe  Thr  Glu  Lys  Asp  Glu  Lys
               290                     295                     300

GAC  TTT  GCT  GCT  TAT  TTG  GCA  TTT  TGT  GGT  ATT  GTT  CTT  CAT  AAT  GCT      962
Asp  Phe  Ala  Ala  Tyr  Leu  Ala  Phe  Cys  Gly  Ile  Val  Leu  His  Asn  Ala
               305                     310                     315

CAG  CTC  TAT  GAG  ACT  TCA  CTG  CTG  GAG  AAC  AAG  AGA  AAT  CAG  GTG  CTG     1010
Gln  Leu  Tyr  Glu  Thr  Ser  Leu  Leu  Glu  Asn  Lys  Arg  Asn  Gln  Val  Leu
               320                     325                     330

CTT  GAC  CTT  GCT  AGT  TTA  ATT  TTT  GAA  GAA  CAA  CAA  TCA  TTA  GAA  GTA     1058
Leu  Asp  Leu  Ala  Ser  Leu  Ile  Phe  Glu  Glu  Gln  Gln  Ser  Leu  Glu  Val
     335                     340                     345

ATT  TTG  AAG  AAA  ATA  GCT  GCC  ACT  ATT  ATC  TCT  TTC  ATG  CAA  GTG  CAG     1106
Ile  Leu  Lys  Lys  Ile  Ala  Ala  Thr  Ile  Ile  Ser  Phe  Met  Gln  Val  Gln
350                     355                     360                     365

AAA  TGC  ACC  ATT  TTC  ATA  GTG  GAT  GAA  GAT  TGC  TCC  GAT  TCT  TTT  TCT     1154
Lys  Cys  Thr  Ile  Phe  Ile  Val  Asp  Glu  Asp  Cys  Ser  Asp  Ser  Phe  Ser
```

|  |  |  |  |  |  |  |  |  |  |  |  |  |  |  |  |
|---|---|---|---|---|---|---|---|---|---|---|---|---|---|---|---|
|  |  |  | 370 |  |  |  |  | 375 |  |  |  |  | 380 |  |  |

```
AGT GTG TTT CAC ATG GAG TGT GAG GAA TTA GAA AAA TCA TCT GAT ACA      1202
Ser Val Phe His Met Glu Cys Glu Glu Leu Glu Lys Ser Ser Asp Thr
            385                     390                 395

TTA ACA AGG GAA CAT GAT GCA AAC AAA ATC AAT TAC ATG TAT GCT CAG      1250
Leu Thr Arg Glu His Asp Ala Asn Lys Ile Asn Tyr Met Tyr Ala Gln
        400                     405                 410

TAT GTC AAA AAT ACT ATG GAA CCA CTT AAT ATC CCA GAT GTC AGT AAG      1298
Tyr Val Lys Asn Thr Met Glu Pro Leu Asn Ile Pro Asp Val Ser Lys
    415                     420                 425

GAT AAA AGA TTT CCC TGG ACA ACT GAA AAT ACA GGA AAT GTA AAC CAG      1346
Asp Lys Arg Phe Pro Trp Thr Thr Glu Asn Thr Gly Asn Val Asn Gln
430                     435                 440                 445

CAG TGC ATT AGA AGT TTG CTT TGT ACA CCT ATA AAA AAT GGA AAG AAG      1394
Gln Cys Ile Arg Ser Leu Leu Cys Thr Pro Ile Lys Asn Gly Lys Lys
                450                 455                 460

AAT AAA GTT ATA GGG GTT TGC CAA CTT GTT AAT AAG ATG GAG GAG AAT      1442
Asn Lys Val Ile Gly Val Cys Gln Leu Val Asn Lys Met Glu Glu Asn
            465                 470                 475

ACT GGC AAG GTT AAG CCT TTC AAC CGA AAT GAC GAA CAG TTT CTG GAA      1490
Thr Gly Lys Val Lys Pro Phe Asn Arg Asn Asp Glu Gln Phe Leu Glu
        480                 485                 490

GCT TTT GTC ATC TTT TGT GGC TTG GGG ATC CAG AAC ACG CAG ATG TAT      1538
Ala Phe Val Ile Phe Cys Gly Leu Gly Ile Gln Asn Thr Gln Met Tyr
    495                 500                 505

GAA GCA GTG GAG AGA GCC ATG GCC AAG CAA ATG GTC ACA TTG GAG GTT      1586
Glu Ala Val Glu Arg Ala Met Ala Lys Gln Met Val Thr Leu Glu Val
510                 515                 520                 525

CTG TCG TAT CAT GCT TCA GCA GCA GAG GAA GAA ACA AGA GAG CTA CAG      1634
Leu Ser Tyr His Ala Ser Ala Ala Glu Glu Glu Thr Arg Glu Leu Gln
                530                 535                 540

TCG TTA GCG GCT GCT GTG GTG CCA TCT GCC CAG ACC CTT AAA ATT ACT      1682
Ser Leu Ala Ala Ala Val Val Pro Ser Ala Gln Thr Leu Lys Ile Thr
            545                 550                 555

GAC TTT AGC TTC AGT GAC TTT GAG CTG TCT GAT CTG GAA ACA GCA CTG      1730
Asp Phe Ser Phe Ser Asp Phe Glu Leu Ser Asp Leu Glu Thr Ala Leu
        560                 565                 570

TGT ACA ATT CGG ATG TTT ACT GAC CTC AAC CTT GTG CAG AAC TTC CAG      1778
Cys Thr Ile Arg Met Phe Thr Asp Leu Asn Leu Val Gln Asn Phe Gln
    575                 580                 585

ATG AAA CAT GAG GTT CTT TGC AGA TGG ATT TTA AGT GTT AAG AAG AAT      1826
Met Lys His Glu Val Leu Cys Arg Trp Ile Leu Ser Val Lys Lys Asn
590                 595                 600                 605

TAT CGG AAG AAT GTT GCC TAT CAT AAT TGG AGA CAT GCC TTT AAT ACA      1874
Tyr Arg Lys Asn Val Ala Tyr His Asn Trp Arg His Ala Phe Asn Thr
                610                 615                 620

GCT CAG TGC ATG TTT GCT GCT CTA AAA GCA GGC AAA ATT CAG AAC AAG      1922
Ala Gln Cys Met Phe Ala Ala Leu Lys Ala Gly Lys Ile Gln Asn Lys
            625                 630                 635

CTG ACT GAC CTG GAG ATA CTT GCA TTG CTG ATT GCT GCA CTA AGC CAC      1970
Leu Thr Asp Leu Glu Ile Leu Ala Leu Leu Ile Ala Ala Leu Ser His
        640                 645                 650

GAT TTG GAT CAC CGT GGT GTG AAT AAC TCT TAC ATA CAG CGA AGT GAA      2018
Asp Leu Asp His Arg Gly Val Asn Asn Ser Tyr Ile Gln Arg Ser Glu
    655                 660                 665

CAT CCA CTT GCC CAG CTT TAC TGC CAT TCA ATC ATG GAA CAC CAT CAT      2066
His Pro Leu Ala Gln Leu Tyr Cys His Ser Ile Met Glu His His His
670                 675                 680                 685

TTT GAC CAG TGC CTG ATG ATT CTT AAT AGT CCA GGC AAT CAG ATT CTC      2114
Phe Asp Gln Cys Leu Met Ile Leu Asn Ser Pro Gly Asn Gln Ile Leu
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 690 |     |     |     |     |     | 695 |     |     |     |     | 700 |      |
| AGT | GGC | CTC | TCC | ATT | GAA | GAA | TAT | AAG | ACC | ACG | TTG | AAA | ATA | ATC | AAG | 2162 |
| Ser | Gly | Leu | Ser | Ile | Glu | Glu | Tyr | Lys | Thr | Thr | Leu | Lys | Ile | Ile | Lys |      |
|     |     |     | 705 |     |     |     | 710 |     |     |     |     |     | 715 |     |     |      |
| CAA | GCT | ATT | TTA | GCT | ACA | GAC | CTA | GCA | CTG | TAC | ATT | AAG | AGG | CGA | GGA | 2210 |
| Gln | Ala | Ile | Leu | Ala | Thr | Asp | Leu | Ala | Leu | Tyr | Ile | Lys | Arg | Arg | Gly |      |
|     |     |     | 720 |     |     |     | 725 |     |     |     |     |     | 730 |     |     |      |
| GAA | TTT | TTT | GAA | CTT | ATA | AGA | AAA | AAT | CAA | TTC | AAT | TTG | GAA | GAT | CCT | 2258 |
| Glu | Phe | Phe | Glu | Leu | Ile | Arg | Lys | Asn | Gln | Phe | Asn | Leu | Glu | Asp | Pro |      |
|     |     |     | 735 |     |     |     | 740 |     |     |     |     |     | 745 |     |     |      |
| CAT | CAA | AAG | GAG | TTG | TTT | TTG | GCA | ATG | CTG | ATG | ACA | GCT | TGT | GAT | CTT | 2306 |
| His | Gln | Lys | Glu | Leu | Phe | Leu | Ala | Met | Leu | Met | Thr | Ala | Cys | Asp | Leu |      |
| 750 |     |     |     |     | 755 |     |     |     |     | 760 |     |     |     |     | 765 |      |
| TCT | GCA | ATT | ACA | AAA | CCC | TGG | CCT | ATT | CAA | CAA | CGG | ATA | GCA | GAA | CTT | 2354 |
| Ser | Ala | Ile | Thr | Lys | Pro | Trp | Pro | Ile | Gln | Gln | Arg | Ile | Ala | Glu | Leu |      |
|     |     |     |     | 770 |     |     |     |     | 775 |     |     |     |     | 780 |     |      |
| GTA | GCA | ACT | GAA | TTT | TTT | GAT | CAA | GGA | GAC | AGA | GAG | AGA | AAA | GAA | CTC | 2402 |
| Val | Ala | Thr | Glu | Phe | Phe | Asp | Gln | Gly | Asp | Arg | Glu | Arg | Lys | Glu | Leu |      |
|     |     |     | 785 |     |     |     | 790 |     |     |     |     |     | 795 |     |     |      |
| AAC | ATA | GAA | CCC | ACT | GAT | CTA | ATG | AAC | AGG | GAG | AAG | AAA | AAC | AAA | ATC | 2450 |
| Asn | Ile | Glu | Pro | Thr | Asp | Leu | Met | Asn | Arg | Glu | Lys | Lys | Asn | Lys | Ile |      |
|     |     | 800 |     |     |     |     | 805 |     |     |     |     |     | 810 |     |     |      |
| CCA | AGT | ATG | CAA | GTT | GGG | TTC | ATA | GAT | GCC | ATC | TGC | TTG | CAA | CTG | TAT | 2498 |
| Pro | Ser | Met | Gln | Val | Gly | Phe | Ile | Asp | Ala | Ile | Cys | Leu | Gln | Leu | Tyr |      |
|     | 815 |     |     |     |     | 820 |     |     |     |     | 825 |     |     |     |     |      |
| GAG | GCC | CTG | ACC | CAC | GTG | TCA | GAG | GAC | TGT | TTC | CCT | TTG | CTA | GAT | GGC | 2546 |
| Glu | Ala | Leu | Thr | His | Val | Ser | Glu | Asp | Cys | Phe | Pro | Leu | Leu | Asp | Gly |      |
| 830 |     |     |     |     | 835 |     |     |     |     | 840 |     |     |     |     | 845 |      |
| TGC | AGA | AAG | AAC | AGG | CAG | AAA | TGG | CAG | GCC | CTT | GCA | GAA | CAG | CAG | GAG | 2594 |
| Cys | Arg | Lys | Asn | Arg | Gln | Lys | Trp | Gln | Ala | Leu | Ala | Glu | Gln | Gln | Glu |      |
|     |     |     |     | 850 |     |     |     |     | 855 |     |     |     |     | 860 |     |      |
| AAG | ATG | CTG | ATT | AAT | GGG | GAA | AGC | GGC | CAG | GCC | AAG | CGG | AAC |     |     | 2636 |
| Lys | Met | Leu | Ile | Asn | Gly | Glu | Ser | Gly | Gln | Ala | Lys | Arg | Asn |     |     |      |
|     |     |     | 865 |     |     |     |     | 870 |     |     |     | 875 |     |     |     |      |
| TGACTCGAG |     |     |     |     |     |     |     |     |     |     |     |     |     |     |     | 2645 |

( 2 ) INFORMATION FOR SEQ ID NO:23:

( i ) SEQUENCE CHARACTERISTICS:
        ( A ) LENGTH: 875 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

|     |     |     |     |     |     |     |     |     |     |     |     |     |     |     |
|-----|-----|-----|-----|-----|-----|-----|-----|-----|-----|-----|-----|-----|-----|-----|
| Met | Glu | Arg | Ala | Gly | Pro | Ser | Phe | Gly | Gln | Arg | Gln | Gln | Gln | Gln |
| 1   |     |     |     | 5   |     |     |     |     | 10  |     |     |     |     | 15  |
| Pro | Gln | Gln | Gln | Lys | Gln | Gln | Arg | Asp | Gln | Asp | Ser | Val | Glu | Ala |
|     |     |     | 20  |     |     |     |     | 25  |     |     |     |     | 30  |     |
| Trp | Leu | Asp | Asp | His | Trp | Asp | Phe | Thr | Phe | Ser | Tyr | Phe | Val | Arg | Lys |
|     |     | 35  |     |     |     |     | 40  |     |     |     |     | 45  |     |     |
| Ala | Thr | Arg | Glu | Met | Val | Asn | Ala | Trp | Phe | Ala | Glu | Arg | Val | His | Thr |
|     | 50  |     |     |     |     | 55  |     |     |     |     | 60  |     |     |     |
| Ile | Pro | Val | Cys | Lys | Glu | Gly | Ile | Arg | Gly | His | Thr | Glu | Ser | Cys | Ser |
| 65  |     |     |     |     | 70  |     |     |     |     | 75  |     |     |     |     | 80  |
| Cys | Pro | Leu | Gln | Gln | Ser | Pro | Arg | Ala | Asp | Asn | Ser | Val | Pro | Gly | Thr |
|     |     |     |     | 85  |     |     |     |     | 90  |     |     |     |     | 95  |     |
| Pro | Thr | Arg | Lys | Ile | Ser | Ala | Ser | Glu | Phe | Asp | Arg | Pro | Leu | Arg | Pro |
|     |     |     | 100 |     |     |     |     | 105 |     |     |     |     | 110 |     |     |

```
Ile  Val  Val  Lys  Asp  Ser  Glu  Gly  Thr  Val  Ser  Phe  Leu  Ser  Asp  Ser
          115                      120                     125

Glu  Lys  Lys  Glu  Gln  Met  Pro  Leu  Thr  Pro  Pro  Arg  Phe  Asp  His  Asp
     130                      135                     140

Glu  Gly  Asp  Gln  Cys  Ser  Arg  Leu  Leu  Glu  Leu  Val  Lys  Asp  Ile  Ser
145                      150                     155                          160

Ser  His  Leu  Asp  Val  Thr  Ala  Leu  Cys  His  Lys  Ile  Phe  Leu  His  Ile
               165                      170                          175

His  Gly  Leu  Ile  Ser  Ala  Asp  Arg  Tyr  Ser  Leu  Phe  Leu  Val  Cys  Glu
               180                      185                     190

Asp  Ser  Ser  Asn  Asp  Lys  Phe  Leu  Ile  Ser  Arg  Leu  Phe  Asp  Val  Ala
          195                      200                     205

Glu  Gly  Ser  Thr  Leu  Glu  Glu  Val  Ser  Asn  Asn  Cys  Ile  Arg  Leu  Glu
     210                      215                     220

Trp  Asn  Lys  Gly  Ile  Val  Gly  His  Val  Ala  Ala  Leu  Gly  Glu  Pro  Leu
225                      230                     235                          240

Asn  Ile  Lys  Asp  Ala  Tyr  Glu  Asp  Pro  Arg  Phe  Asn  Ala  Glu  Val  Asp
               245                      250                     255

Gln  Ile  Thr  Gly  Tyr  Lys  Thr  Gln  Ser  Ile  Leu  Cys  Met  Pro  Ile  Lys
               260                      265                     270

Asn  His  Arg  Glu  Glu  Val  Val  Gly  Val  Ala  Gln  Ala  Ile  Asn  Lys  Lys
          275                      280                     285

Ser  Gly  Asn  Gly  Gly  Thr  Phe  Thr  Glu  Lys  Asp  Glu  Lys  Asp  Phe  Ala
     290                      295                     300

Ala  Tyr  Leu  Ala  Phe  Cys  Gly  Ile  Val  Leu  His  Asn  Ala  Gln  Leu  Tyr
305                      310                     315                          320

Glu  Thr  Ser  Leu  Leu  Glu  Asn  Lys  Arg  Asn  Gln  Val  Leu  Leu  Asp  Leu
               325                      330                     335

Ala  Ser  Leu  Ile  Phe  Glu  Glu  Gln  Gln  Ser  Leu  Glu  Val  Ile  Leu  Lys
               340                      345                     350

Lys  Ile  Ala  Ala  Thr  Ile  Ile  Ser  Phe  Met  Gln  Val  Gln  Lys  Cys  Thr
          355                      360                     365

Ile  Phe  Ile  Val  Asp  Glu  Asp  Cys  Ser  Asp  Ser  Phe  Ser  Ser  Val  Phe
     370                      375                     380

His  Met  Glu  Cys  Glu  Glu  Leu  Glu  Lys  Ser  Ser  Asp  Thr  Leu  Thr  Arg
385                      390                     395                          400

Glu  His  Asp  Ala  Asn  Lys  Ile  Asn  Tyr  Met  Tyr  Ala  Gln  Tyr  Val  Lys
               405                      410                     415

Asn  Thr  Met  Glu  Pro  Leu  Asn  Ile  Pro  Asp  Val  Ser  Lys  Asp  Lys  Arg
               420                      425                     430

Phe  Pro  Trp  Thr  Thr  Glu  Asn  Thr  Gly  Asn  Val  Asn  Gln  Gln  Cys  Ile
          435                      440                     445

Arg  Ser  Leu  Leu  Cys  Thr  Pro  Ile  Lys  Asn  Gly  Lys  Lys  Asn  Lys  Val
     450                      455                     460

Ile  Gly  Val  Cys  Gln  Leu  Val  Asn  Lys  Met  Glu  Glu  Asn  Thr  Gly  Lys
465                      470                     475                          480

Val  Lys  Pro  Phe  Asn  Arg  Asn  Asp  Glu  Gln  Phe  Leu  Glu  Ala  Phe  Val
               485                      490                     495

Ile  Phe  Cys  Gly  Leu  Gly  Ile  Gln  Asn  Thr  Gln  Met  Tyr  Glu  Ala  Val
               500                      505                     510

Glu  Arg  Ala  Met  Ala  Lys  Gln  Met  Val  Thr  Leu  Glu  Val  Leu  Ser  Tyr
          515                      520                     525

His  Ala  Ser  Ala  Ala  Glu  Glu  Glu  Thr  Arg  Glu  Leu  Gln  Ser  Leu  Ala
```

```
                    530                           535                           540
Ala  Ala  Val  Val  Pro  Ser  Ala  Gln  Thr  Leu  Lys  Ile  Thr  Asp  Phe  Ser
545                           550                           555                           560

Phe  Ser  Asp  Phe  Glu  Leu  Ser  Asp  Leu  Glu  Thr  Ala  Leu  Cys  Thr  Ile
                              565                           570                           575

Arg  Met  Phe  Thr  Asp  Leu  Asn  Leu  Val  Gln  Asn  Phe  Gln  Met  Lys  His
                    580                           585                           590

Glu  Val  Leu  Cys  Arg  Trp  Ile  Leu  Ser  Val  Lys  Lys  Asn  Tyr  Arg  Lys
               595                           600                           605

Asn  Val  Ala  Tyr  His  Asn  Trp  Arg  His  Ala  Phe  Asn  Thr  Ala  Gln  Cys
          610                           615                           620

Met  Phe  Ala  Ala  Leu  Lys  Ala  Gly  Lys  Ile  Gln  Asn  Lys  Leu  Thr  Asp
625                           630                           635                           640

Leu  Glu  Ile  Leu  Ala  Leu  Leu  Ile  Ala  Ala  Leu  Ser  His  Asp  Leu  Asp
                    645                           650                           655

His  Arg  Gly  Val  Asn  Asn  Ser  Tyr  Ile  Gln  Arg  Ser  Glu  His  Pro  Leu
               660                           665                           670

Ala  Gln  Leu  Tyr  Cys  His  Ser  Ile  Met  Glu  His  His  His  Phe  Asp  Gln
          675                           680                           685

Cys  Leu  Met  Ile  Leu  Asn  Ser  Pro  Gly  Asn  Gln  Ile  Leu  Ser  Gly  Leu
     690                           695                           700

Ser  Ile  Glu  Glu  Tyr  Lys  Thr  Thr  Leu  Lys  Ile  Ile  Lys  Gln  Ala  Ile
705                           710                           715                           720

Leu  Ala  Thr  Asp  Leu  Ala  Leu  Tyr  Ile  Lys  Arg  Arg  Gly  Glu  Phe  Phe
                    725                           730                           735

Glu  Leu  Ile  Arg  Lys  Asn  Gln  Phe  Asn  Leu  Glu  Asp  Pro  His  Gln  Lys
               740                           745                           750

Glu  Leu  Phe  Leu  Ala  Met  Leu  Met  Thr  Ala  Cys  Asp  Leu  Ser  Ala  Ile
          755                           760                           765

Thr  Lys  Pro  Trp  Pro  Ile  Gln  Gln  Arg  Ile  Ala  Glu  Leu  Val  Ala  Thr
     770                           775                           780

Glu  Phe  Phe  Asp  Gln  Gly  Asp  Arg  Glu  Arg  Lys  Glu  Leu  Asn  Ile  Glu
785                           790                           795                           800

Pro  Thr  Asp  Leu  Met  Asn  Arg  Glu  Lys  Lys  Asn  Lys  Ile  Pro  Ser  Met
                    805                           810                           815

Gln  Val  Gly  Phe  Ile  Asp  Ala  Ile  Cys  Leu  Gln  Leu  Tyr  Glu  Ala  Leu
               820                           825                           830

Thr  His  Val  Ser  Glu  Asp  Cys  Phe  Pro  Leu  Leu  Asp  Gly  Cys  Arg  Lys
          835                           840                           845

Asn  Arg  Gln  Lys  Trp  Gln  Ala  Leu  Ala  Glu  Gln  Gln  Glu  Lys  Met  Leu
     850                           855                           860

Ile  Asn  Gly  Glu  Ser  Gly  Gln  Ala  Lys  Arg  Asn
865                           870                           875
```

CYCLIC GMP-BINDING, CYCLIC GMP-SPECIFIC PHOSPHODIESTERASE MATERIALS AND METHODS

This is a Rule 62 file wrapper continuation of U.S. application Ser. No. 08/068,051, filed May 27, 1993, now abandoned.

Experimental work described herein was supported in part by Research Grants GM15731, DK21723, DK40029 and GM41269 and the Medical Scientist Training Program Grant GM07347 awarded by the National Institutes of Health. The United States government has certain rights in the invention.

FIELD OF THE INVENTION

The present invention relates generally to a cyclic guanosine monophosphate-binding, cyclic guanosine monophosphate-specific phosphodiesterase designated cGB-PDE and more particularly to novel purified and isolated polynucleotides encoding cGB-PDE polypeptides, to methods and materials for recombinant production of cGB-PDE polypeptides, and to methods for identifying modulators of cGB-PDE activity.

BACKGROUND

Cyclic nucleotide phosphodiesterases (PDEs) that catalyze the hydrolysis of 3'5' cyclic nucleotides such as cyclic guanosine monophosphate (cGMP) and cyclic adenosine monophosphate (cAMP) to the corresponding nucleoside 5' monophosphates constitute a complex family of enzymes. By mediating the intracellular concentration of the cyclic nucleotides, the PDE isoenzymes function in signal transduction pathways involving cyclic nucleotide second messengers.

A variety of PDEs have been isolated from different tissue sources and many of the PDEs characterized to date exhibit differences in biological properties including physicochemical properties, substrate specificity, sensitivity to inhibitors, immunological reactivity and mode of regulation. [See Beavo et al., *Cyclic Nucleotide Phosphodiesterases: Structure, Regulation and Drug Action*, John Wiley & Sons, Chichester, U.K. (1990)] Comparison of the known amino acid sequences of various PDEs indicates that most PDEs are chimeric multidomain proteins that have distinct catalytic and regulatory domains. [See Charbonneau, pp. 267–296 in Beavo et al., supra] All mammalian PDEs characterized to date share a sequence of approximately 250 amino acid residues in length that appears to comprise the catalytic site and is located in the carboxyl terminal region of the enzyme. PDE domains that interact with allosteric or regulatory molecules are thought to be located within the amino-terminal regions of the isoenzymes. Based on their biological properties, the PDEs may be classified into six general families: the $Ca^{2+}$/calmodulin-stimulated PDEs (Type I), the cGMP-stimulated PDEs (Type II), the cGMP-inhibited PDEs (Type III), the cAMP-specfic PDEs (Type IV), the cGMP-specific phosphodiesterase cGB-PDE (Type V) which is the subject of the present invention and the cGMP-specific photoreceptor PDEs (Type VI).

The cGMP-binding PDEs (Type II, Type V and Type VI PDEs), in addition to having a homologous catalytic domain near their carboxyl terminus, have a second conserved sequence which is located closer to their amino terminus and which may comprise an allosteric cGMP-binding domain. See Charbonneau et al., *Proc. Natl. Acad. Sci. USA*, 87: 288–292 (1990).

The Type II cGMP-stimulated PDEs (cGs-PDEs) are widely distributed in different tissue types and are thought to exist as homodimers of 100–105 kDa subunits. The cGs-PDEs respond under physiological conditions to elevated cGMP concentrations by increasing the rate of cAMP hydrolysis. The amino acid sequence of a bovine heart cGs-PDE and a partial cDNA sequence of a bovine adrenal cortex cGS-PDE are reported in LeTrong et al., *Biochemistry*, 29: 10280–10288 (1990) and full length bovine adrenal and human fetal brain cGS-PDE cDNA sequences are described in Patent Cooperation Treaty International Publication No. WO 92/18541 published on Oct. 29, 1992. The full length bovine adrenal cDNA sequence is also described in Sonnenburg et al., *J. Biol. Chem.*, 266: 17655–17661 (1991).

The photoreceptor PDEs and the cGB-PDE have been described as cGMP-specific PDEs because they exhibit a 50-fold or greater selectivity for hydrolyzing cGMP over cAMP.

The photoreceptor PDEs are the rod outer segment PDE (ROS-PDE) and the cone PDE (COS-PDE). The holoenzyme structure of the ROS-PDE consists of two large subunits at (88 kDa) and β (84 kDa) which are both catalytically active and two smaller γ regulatory subunits (both 11 kDa). A soluble form of the ROS-PDE has also been identified which includes α,β, and γ subunits and δ subunit (15 kDa) that appears to be identical to the COS-PDE 15 kDa subunit. A full-length cDNA corresponding to the bovine membrane-associated ROS-PDE α subunit is described in Ovchinnikov et al., *FEBS Lett.*, 223: 169–173 (1987) and a full length cDNA corresponding to the bovine rod outer segment PDE β subunit is described in Lipkin et al., *J. Biol. Chem.*, 265: 12955–12959 (1990). Ovchinnikov et al., *FEBS Lett.*, 204: 169–173 (1986) presents a full-length cDNA corresponding to the bovine ROS-PDE γ subunit and the amino acid sequence of the δ subunit. Expression of the ROS-PDE has also been reported in brain in Collins et al., *Genomics*, 13: 698–704 (1992). The COS-PDE is composed of two identical α' (94 kDa) subunits and three smaller subunits of 11 kDa, 13 kDa and 15 kDa. A full-length cDNA corresponding to the bovine COS-PDE α' subunit is reported in Li et al., *Proc. Natl. Acad. Sci. USA*, 87: 293–297 (1990).

cGB-PDE has been purified to homogeneity from rat [Francis et al., *Methods Enzymol.*, 159: 722–729 (1988)] and bovine lung tissue [Thomas et al., *J. Biol. Chem.*, 265: 14964–14970 (1990), hereinafter "Thomas I"]. The presence of this or similar enzymes has been reported in a variety of tissues and species including rat and human platelets [Hamer et al., *Adv. Cyclic Nucleotide Protein Phosphorylation Res.*, 16: 119–136 (1984)], rat spleen [Coquil et al., *Biochem. Biophys. Res. Commun.*, 127: 226–231 (1985)], guinea pig lung [Davis et al., *J. Biol. Chem.*, 252: 4078–4084 (1977)], vascular smooth muscle [Coquil et al., *Biochem. Biophys. Acta*, 631: 148–165 (1980)], and sea urchin sperm [Francis et al., *J. Biol. Chem.*, 255: 620–626 (1979)]. cGB-PDE may be a homodimer comprised of two 93 kDa subunits. [See Thomas I, supra] cGB-PDE has been shown to contain a single site not found in other known cGMP-binding PDEs which is phosphorylated by cGMP-dependent protein kinase (cGK) and, with a lower affinity, by cAMP-dependent protein kinase (cAK). [See Thomas et al., *J. Biol. Chem.*, 265: 14971–14978 (1990), hereinafter "Thomas II"] The primary amino acid sequence of the phosphorylation site and of the amino-terminal end of a fragment generated by chymotryptic digestion of cGB-PDE are described in Thomas II, supra, and Thomas I, supra, respectively. However, the majority of the amino acid sequence of cGB-PDE has not previously been described.

Various inhibitors of different types of PDEs have been described in the literature. Two inhibitors that exhibit some specificity for Type V PDEs are zaprinast and dipyridamole. See Francis et at., pp. 117–140 in Beavo et al., supra.

Elucidation of the DNA and amino acid sequences encoding the cGB-PDE and production of cGB-PDE polypeptide by recombinant methods would provide information and material to allow the identification of novel agents that selectively modulate the activity of the cGB-PDEs. The recognition that there are distinct types or families of PDE isoenzymes and that different tissues express different complements of PDEs has led to an interest in the development of PDE modulators which may have therapeutic indications for disease states that involve signal transduction pathways utilizing cyclic nucleotides as second messengers. Various selective and non-selective inhibitors of PDE activity are discussed in Murray et at., Biochem. Soc. Trans., 20(2): 460–464 (1992). Development of PDE modulators without the ability to produce a specific PDE by recombinant DNA techniques is difficult because all PDEs catalyze the same basic reaction, have overlapping substrate specificities and occur only in trace amounts. As a result, purification to homogeneity of many PDEs is a tedious and difficult process.

There thus continues to exist a need in the art for DNA and amino acid sequence information for the cGB-PDE, for methods and materials for the recombinant production of cGB-PDE polypeptides and for methods for identifying specific modulators of cGB-PDE activity.

SUMMARY OF THE INVENTION

The present invention provides novel purified and isolated polynucleotides (e.g., DNA sequences and RNA transcripts including splice variants thereof) encoding the cGMP-binding, cGMP-specific PDE designated cGB-PDE. Preferred DNA sequences of the invention include genomic and cDNA sequences as well as wholly or partially chemically synthesized DNA sequences. DNA sequences encoding cGB-PDE that are set out in SEQ ID NO: 9 or 20 and DNA sequences which hybridize thereto under stringent conditions or DNA sequences which would hybridize thereto but for the redundancy of the genetic code are contemplated by the invention. Also contemplated by the invention are biological replicas (i.e., copies of isolated DNA sequences made in vivo or in vitro) of DNA sequences of the invention. Autonomously replicating recombinant constructions such as plasmid and viral DNA vectors incorporating cGB-PDE sequences and especially vectors wherein DNA encoding cGB-PDE is operatively linked to an endogenous or exogenous expression control DNA sequence and a transcriptional terminator are also provided. Specifically illustrating expression plasmids of the invention is the plasmid hcgbmet156-2 6n in E. coli strain JM109 which was deposited with the American Type Culture Collection (ATCC), 12301 Parklawn Drive, Rockville, Md. 20852, on May 4, 1993 as Accession No. 69296.

According to another aspect of the invention, host cells including procaryotic and eucaryotic cells, are stably transformed with DNA sequences of the invention in a manner allowing the desired polypeptides to be expressed therein. Host cells expressing cGB-PDE products can serve a variety of useful purposes. Such cells constitute a valuable source of immunogen for the development of antibody substances specifically immunoreactive with cGB-PDE. Host cells of the invention are conspicuously useful in methods for the large scale production of cGB-PDE polypeptides wherein the cells are grown in a suitable culture medium and the desired polypeptide products are isolated from the cells or from the medium in which the cells are grown by, for example, immunoaffinity purification.

cGB-PDE products may be obtained as isolates from natural cell sources or may be chemically synthesized, but are preferably produced by recombinant procedures involving host cells of the invention. Use of mammalian host cells is expected to provide for such post-translational modifications (e.g., glycosylation, truncation, lipidation and tyrosine, serine or threonine phosphorylation) as may be needed to confer optimal biological activity on recombinant expression products of the invention. cGB-PDE products of the invention may be full length polypeptides, fragments or variants. Variants may comprise cGB-PDE polypeptide analogs wherein one or more of the specified (i.e., naturally encoded) amino acids is deleted or replaced or wherein one or more nonspecified amino acids are added: (1) without loss of one or more of the biological activities or immunological characteristics specific for cGB-PDE; or (2) with specific disablement of a particular biological activity of cGB-PDE.

Also comprehended by the present invention are antibody substances (e.g., monoclonal and polyclonal antibodies, single chain antibodies, chimeric antibodies, CDR-grafted antibodies and the like) and other binding proteins specific for cGB-PDE. Specific binding proteins can be developed using isolated or recombinant cGB-PDE or cGB-PDE variants or cells expressing such products. Binding proteins are useful, in turn, in compositions for immunization as well as for purifying cGB-PDE polypeptides and detection or quantification of cGB-PDE polypeptides in fluid and tissue samples by known immunogical procedures. They are also manifestly useful in modulating (i.e., blocking, inhibiting or stimulating) biochemical activities of cGB-PDE, especially those activities involved in signal transduction. Anti-idiotypic antibodies specific for anti-cGB-PDE antibody substances are also contemplated.

The scientific value of the information contributed through the disclosures of DNA and amino acid sequences of the present invention is manifest. As one series of examples, knowledge of the sequence of a cDNA for cGB-PDE makes possible the isolation by DNA/DNA hybridization of genomic DNA sequences encoding cGB-PDE and specifying cGB-PDE expression control regulatory sequences such as promoters, operators and the like. DNA/DNA hybridization procedures carried out with DNA sequences of the invention under stringent conditions are likewise expected to allow the isolation of DNAs encoding allelic variants of cGB-PDE, other structurally related proteins sharing one or more of the biochemical and/or immunological properties specific to cGB-PDE, and non-human species proteins homologous to cGB-PDE. Polynucleotides of the invention when suitably labelled are useful in hybridization assays to detect the capacity of cells to synthesize cGB-PDE. Polynucleotides of the invention may also be the basis for diagnostic methods useful for identifying a genetic alteration(s) in the cGB-PDE locus that underlies a disease state or states. Also made available by the invention are anti-sense polynucleotides relevant to regulating expression of cGB-PDE by those cells which ordinarily express the same.

The DNA and amino acid sequence information provided by the present invention also makes possible the systematic analysis of the structure and function of cGB-PDE and definition of those molecules with which it will interact.

Agents that modulate cGB-PDE activity may be identified by incubating a putative modulator with lysate from eucaryotic cells expressing recombinant cGB-PDE and determining the effect of the putative modulator on cGB-PDE phosphodiesterase activity. In a preferred embodiment the eucaryotic cell lacks endogenous cyclic nucleotide phosphodiesterase activity. Specifically illustrating such a eucaryotic cell is the yeast strain YKS45 which was deposited with the ATCC on May 19, 1993 as Accession No. 74225. The selectivity of a compound that modulates the activity of the cGB-PDE can be evaluated by comparing its activity on the cGB-PDE to its activity on other PDE isozymes. The combination of the recombinant cGB-PDE products of the invention with other recombinant PDE products in a series of independent assays provides a system for developing selective modulators of cGB-PDE.

Selective modulators may include, for example, antibodies and other proteins or peptides which specifically bind to the cGB-PDE or cGB-PDE nucleic acid, oligonucleotides which specifically bind to the cGB-PDE or cGB-PDE nucleic acid and other non-peptide compounds (e.g., isloated or synthetic organic molecules) which specifically react with cGB-PDE or cGB-PDE nucleic acid. Mutant forms of cGB-PDE which affect the enzymatic activity or cellular localization of the wild-type cGB-PDE are also contemplated by the invention. Presently preferred targets for the development of selective modulators include, for example: (1) the regions of the cGB-PDE which contact other proteins and/or localize the cGB-PDE within a cell, (2) the regions of the cGB-PDE which bind substrate, (3) the allosteric cGMP-binding site(s) of cGB-PDE, (4) the phosphorylation site(s) of cGB-PDE and (5) the regions of the cGB-PDE which are involved in dimerization of cGB-PDE subunits. Modulators of cGB-PDE activity may be therapeutically useful in treatment of a wide range of diseases and physiological conditions.

BRIEF DESCRIPTION OF THE DRAWINGS

Numerous other aspects and advantages of the present invention will be apparent upon consideration of the following detailed description thereof, reference being made to the drawing wherein:

FIGS. 1A–1C are an alignment of the conserved catalytic domains of several PDE isoenzymes wherein residues which are identical in all PDEs listed are indicated by their one letter amino acid abbreviation in the "conserved" line, residues which are identical in the cGB-PDE and photoreceptor PDEs only are indicated by a star in the "conserved" line and gaps introduced for optimum alignment are indicated by periods;

FIGS. 2A–2C are an alignment of the cGMP-binding domains of several PDE isoenzymes wherein residues which are identical in all PDEs listed are indicated by their one letter amino acid abbreviation in the "conserved" line and gaps introduced for optimum alignment are indicated by periods;

FIG. 3 is an alignment of internally homologous repeats from several PDE isoenzymes wherein residues identical in each repeat A and B from all cGMP-binding PDEs listed are indicated by their one letter amino acid abbreviation in the "conserved" line and stars in the "conserved" line represent positions in which all residues are chemically conserved;

DETAILED DESCRIPTION

Figure 4:
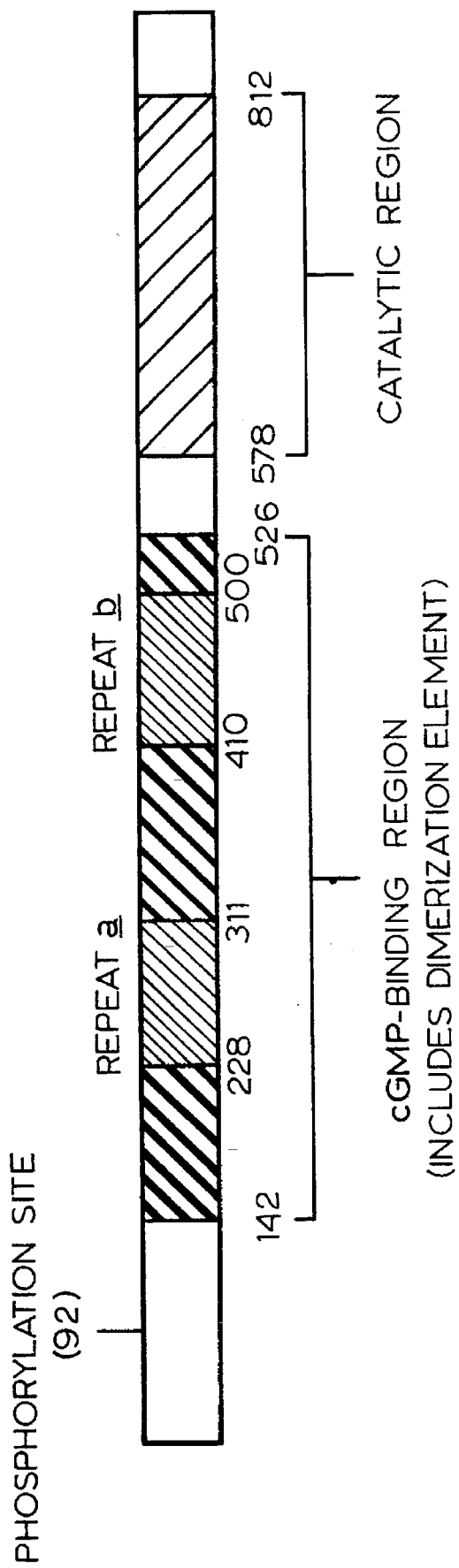
FIG. 4 schematically depicts the domain organization of cGB-PDE.

The following examples illustrate the invention. Example 1 describes the isolation of a bovine cGB-PDE cDNA fragment by PCR and subsequent isolation of a full length cGB-PDE cDNA using the PCR fragment as a probe. Example 2 presents an analysis of the relationship of the bovine cGB-PDE amino acid sequence to sequences reported for various other PDEs. Northern blot analysis of cGB-PDE mRNA in various bovine tissues is presented in Example 3. Expression of the bovine cGB-PDE cDNA in COS cells is described in Example 4. Example 5 presents results of assays of the cGB-PDE COS cell expression product for phosphodiesterase activity and cGMP-binding activity. Example 6 describes the isolation of human cDNAs homologous to the bovine cGB-PDE cDNA. The expression of a human cGB-PDE cDNA in yeast cells is presented in Example 7. RNase protection assays to detect cGB-PDE in human tissues are described in Example 8. Example 9 describes the bacterial expression of human cGB-PDE cDNA and the development of antibodies reactive with the bacterial cGB-PDE expression product. Example 10 relates to utlilizing recombinant cGB-PDE products of the invention to develop agents that selectively modulate the biological activities of cGB-PDE.

EXAMPLE 1

The polymerase chain reaction (PCR) was utilized to isolate a cDNA fragment encoding a portion of cGB-PDE from bovine lung first strand cDNA. Fully degenerate sense and antisense PCR primers were designed based on the partial cGB-PDE amino acid sequence described in Thomas I, supra, and novel partial amino acid sequence information.

A. Purification of cGB-PDE Protein cGB-PDE was purified as described in Thomas I, supra, or by a modification of that method as described below.

Fresh bovine lungs (5–10 kg) were obtained from a slaughterhouse and immediately placed on ice. The tissue was ground and combined with cold PEM buffer (20mM sodium phosphate, pH 6.8, containing 2 mM EDTA and 25 mM β-mercaptoethanol). After homogenization and centrifugation, the resulting supernatant was incubated with 4–7 liters of DEAE-cellulose (Whatman, UK) for 3–4 hours. The DEAE slurry was then filtered under vacuum and rinsed with multiple volumes of cold PEM. The resin was poured into a glass column and washed with three to four volumes of PEM. The protein was eluted with 100mM NaCl in PEM and twelve 1-liter fractions were collected. Fractions were assayed for IBMX-stimulated cGMP binding and cGMP phosphodiesterase activities by standard procedures described in Thomas et al., supra. Appropriate fractions were pooled, diluted 2-fold with cold, deionized water and subjected to Blue Sepharose® CL-6B (Pharmacia LKB Biotechnology Inc., Piscataway, N.J.) chromatography. Zinc chelate affinity adsorbent chromatography was then performed using either an agarose or Sepharose-based gel matrix. The resulting protein pool from the zinc chelation step treated as described in the Thomas I, supra, or was subjected to a modified purification procedure.

As decribed in Thomas I, supra, the protein pool was applied in multiple loads to an HPLC Bio-Sil TSK-545 DEAE column (150×21.5 mm) (BioRad Laboratories, Hercules, Calif.) equilibrated in PEM at 4° C. After an equilibration period, a 120-ml wash of 50mM NaCl in PEM was followed by a 120-ml linear gradient (50–200mM NaCl in PEM) elution at a flow rate of 2 ml/minute. Appropriate fractions were pooled and concentrated in dialysis tubing against Sephadex G-200 (Boehringer Mannheim Biochemicals, UK) to a final volume of 1.5 ml. The concentrated cGB-PDE pool was applied to an HPLC gel filtration column (Bio-Sil TSK-250, 500×21.5 mm) equilibrated in 100 mM sodium phosphate, pH 6.8, 2 mM EDTA, 25 mM β-mercaptoethanol and eluted with a flow rate of 2 ml/minute at 4 ° C.

If the modified, less cumbersome procedure was performed, the protein pool was dialyzed against PEM for 2 hours and loaded onto a 10 ml preparative DEAE Sephacel column (Pharmacia) equilibrated in PEM buffer. The protein was eluted batchwise with 0.5M NaCl in PEM, resulting in an approximately 10–15 fold concentration of protein. The concentrated protein sample was loaded onto an 800 ml (2.5 cm ×154 cm) Sephacryl S400 gel filtration column (Boehringer) equilibrated in 0.1M NaCl in PEM, and eluted at a flow rate of 1.7 ml/minute.

The purity of the protein was assessed by Coomassie staining after sodium dodecyl sulfate-polyacrylamide gel electrophoresis (SDS-PAGE). Approximately 0.5–3.0 mg of pure cGB-PDE were obtained per 10 kg bovine lung.

Rabbit polyclonal antibodies specific for the purified bovine cGB-PDE were generated by standard procedures.

B. Amino Acid Sequencing of cGB-PDE cGB-PDE phosphorylated with [$^{32}$P]ATP and was then digested with protease to yield $^{32}$P-labelled phosphopeptides. Approximately 100 μg of purified cGB-PDE was phosphorylated in a reaction mixture containing 9 mM MgCl$_2$, 9 μM [$^{32}$P]ATP, 10 μM cGMP, and 4.2 μg purified bovine catalytic subunit of cAMP-dependent protein kinase (cAK) in a final volume of 900 μl. Catalytic subunit of cAK was prepared according to the method of Flockhart et al., pp. 209–215 in Marangos et al., Brain Receptor Methodologies, Part A, Academic Press, Orlando, Fla. (1984). The reaction was incubated for 30 minutes at 30° C., and stopped by addition of 60 μl of 200 mM EDTA.

To obtain a first peptide sequence from cGB-PDE, 3.7 μl of a 1 mg/ml solution of a α-chymotrypsin in KPE buffer (10 mM potassium phosphate, pH 6.8, with 2 mM EDTA) was added to 100 μg purified, phosphorylated cGB-PDE and the mixture was incubated for 30 minutes at 30° C. Proteolysis was stopped by addition of 50 μl of 10% SDS and 25 μl of β-mercaptoethanol. The sample was boiled until the volume was reduced to less than 400 μl, and was loaded onto an 8% preparative SDS-polyacrylamide gel and subjected to electrophoresis at 50 mAmps. The separated digestion products were electroblotted onto Immobilon polyvinylidene difluoride (Millipore, Bedford, Mass.), according to the method of Matsudaira, J. Biol. Chem, 262: 10035–10038 (1987). Transferred protein was identified by Coomassie Blue staining, and a 50 kDa band was excised from the membrane for automated gas-phase amino acid sequencing. The sequence of the peptide obtained by the α-chymotryptic digestion procedure is set out below as SEQ ID NO: 1.

SEQ ID NO: 1
REXDANRINYMYAQYVKNTM

A second sequence was obtained from a cGB-PDE peptide fragment generated by V8 proteolysis. Approximately 200 μg of purified cGB-PDE was added to 10 mM MgCl$_2$, 10 μM [$^{32}$P]ATP, 100 μM cGMP, and 1 μg/ml purified catalytic subunit of cAK in a final volume of 1.4 ml. The reaction was incubated for 30 minutes at 30° C., and was terminated by the addition of 160 μl of 0.2M EDTA. Next, 9 μl of 1 mg/ml Staphylococcal aureus V8 protease (International Chemical Nuclear Biomedicals, Costa Mesa, Calif.) diluted in KPE was added, followed by a 15 minute incubation at 30 ° C. Proteolysis was stopped by addition of 88 μl of 10% SDS and 45 μl β-mercaptoethanol. The digestion products were separated by electrophoresis on a preparative 10% SDS-polyacrylamide gel run at 25 mAmps for 4.5 hours. Proteins were electroblotted and stained as described above. A 28 kDa protein band was excised from the membrane and subjected to automated gas-phase amino acid sequencing. The sequence obtained is set out below as SEQ ID NO: 2.

SEQ ID NO: 2
QSLAAAVVP

C. PCR Amplification of Bovine cDNA

The partial amino acid sequences utilized to design primers (SEQ ID NO: 3, below, and amino acids 9–20 of SEQ ID NO: 1) and the sequences of the corresponding PCR primers (in IUPAC nomenclature) are set below wherein SEQ ID NO: 3 is the sequence reported in Thomas I, supra.

| F D N D E G E Q | SEQ ID NO: 3 |

| 5' TTY GAY AAY GAY GAR GGN GAR CA 3' | (SEQ ID NO: 4) |

| 3' AAR CTR TTR CTR CTY CCN CTY GT 5' | (SEQ ID NO: 5) |

| Amino acids 9–20, | SEQ ID NO: 1 |
| N Y M Y A Q Y V K N T M | |

5' AAY TAY ATG TAY GCN CAR TAY GT 3'  (SEQ ID NO: 6)

3' TTR ATR TAC ATR CGN GTY ATR CA 5'  (SEQ ID NO: 7)

3' TTR ATR TAC ATR CGN GTY ATR CAN TTY TTR TGN TAC 5'  (SEQ ID NO: 8)

The sense and antisense primers, synthesized using an Applied Biosystems Model 380A DNA Synthesizer (Foster City, Calif.), were used in all possible combinations to amplify cGB-PDE-specific sequences from bovine lung first strand cDNA as described below.

After ethanol precipitation, pairs of oligonucleotides were combined (SEQ ID NO: 4 or 5 combined with SEQ ID NOs: 6, 7 or 8) at 400 nM each in a PCR reaction. The reaction was run using 50 ng first strand bovine lung cDNA (generated using AMV reverse transcriptase and random primers on oligo dT selected bovine lung mRNA), 200 µM dNTPs, and 2 units of Taq polymerase. The initial denaturation step was carried out at 94° C. for 5 minutes, followed by 30 cycles of a 1 minute denaturation step at 94° C., a two minute annealing step at 50° C., and a 2 minute extension step at 72° C. PCR was performed using a Hybaid Thermal Reactor (ENK Scientific Products, Saratoga, Calif.) and products were separated by gel electrophoresis on a 1% low melting point agarose gel run in 40 mM Tris-acetate, 2 mM EDTA. A weak band of about 800–840 bp was seen with the primers set out in SEQ ID NOs: 4 and 7 and with primers set out in SEQ ID NOs: 4 and 8. None of the other primer pairs yielded visible bands. The PCR product generated by amplification with the primers set out in SEQ ID NOs: 4 and 7 was isolated using the Gene Clean® (Bio101, La Jolla, Calif.) DNA purification kit according to the manufacturer's protocol. The PCR product (20 ng) was ligated into 200 ng of linearized pBluescript KS(+) (Stratagene, La Jolla, Calif.), and the resulting plasmid construct was used to transform E. coli XL1 Blue cells (Stratagene Cloning Systems, La Jolla, Calif.). Putative transformation positives were screened by sequencing. The sequences obtained were not homologous to any known PDE sequence or to the known partial cGB-PDE sequences.

PCR was performed again on bovine lung first strand cDNA using the primers set out in SEQ ID NOs: 4 and 7. A clone containing a 0.8 Kb insert with a single large open reading frame was identified. The open reading frame encoded a polypeptide that included the amino acids KNTM (amino acids 17–20 of SEQ ID NO: 1 which were not utilized to design the primer sequence which is set out in SEQ ID NO: 7) and that possessed a high degree of homology to the deduced amino acid sequences of the cGs-, ROS- and COS-PDEs. The clone identified corresponds to nucleotides 489–1312 of SEQ ID NO: 9.

D. Construction and Hybridization Screening Of a Bovine cDNA Library

In order to obtain a cDNA encoding a full-length cGB-PDE, a bovine lung cDNA library was screened using the $^{32}$P-labelled PCR-generated cDNA insert as a probe.

Polyadenylated RNA was prepared from bovine lung as described Sonnenburg et al., J. Biol. Chem., 266: 17655–17661 (1991). First strand cDNA was synthesized using AMV reverse transcriptase (Life Sciences, St. Petersburg, Fla.) with random hexanucleotide primers as described in Ausubel et al., Current Protocols in Molecular Biology, John Wiley & Sons, New York (1987). Second strand cDNA was synthesized using E. coli DNA polymerase I in the presence of E. coli DNA ligase and E. coli RNAse H. Selection of cDNAs larger than 500 bp was performed by Sepharose® CL-4B (Millipore) chromatography. EcoRI adaptors (Promega, Madison, Wis.) were ligated to the cDNA using T4 DNA ligase. Following heat inactivation of the ligase, the cDNA was phosphorylated using T4 polynucleotide kinase. Unligated adaptors were removed by Sepharose® CL-4B chromatography (Pharmacia, Piscataway, N.J.). The cDNA was ligated into EcoRI-digested, dephosphorylated lambda Zap®II arms (Stratagene) and packaged with Gigapack® Gold (Stratagene) extracts according to the manufacturer's protocol. The titer of the unamplified library was $9.9 \times 10^5$ with 18% nonrecombinants. The library was amplified by plating 50,000 plaque forming units (pfu) on to twenty 150 mm plates, resulting in a final titer of $5.95 \times 10^6$ pfu/ml with 21% nonrecombinants.

The library was plated on twenty-four 150 mm plates at 50,000 pfu/plate, and screened with the $^{32}$P-labelled cDNA clone. The probe was prepared using the method of Feinberg et al., Anal Biochem., 137: 266–267 (1984), and the $^{32}$P-labelled DNA was purified using Elutip-D® columns (Schleicher and Schuell Inc., Keene, N.H.) using the manufacturer's protocol. Plaque-lifts were performed using 15 cm nitrocellulose filters. Following denaturation and neutralization, DNA was fixed onto the filters by baking at 80° C. for 2 hours. Hybridization was carried out at 42° C. overnight in a solution containing 50% formamide, 5× SSC (0.75M NaCl, 0.75M sodium titrate, pH 7), 25 mM sodium phosphate (pH 7.0), 2× Denhardt's solution, 10% dextran sulfate, 90 µg/ml yeast tRNA, and approximately $10^6$ cpm/ml $^{32}$P-labelled probe ($5 \times 10^8$ cpm/µg). The filters were washed twice in 0.1× SSC, 0.1% SDS at room temperature for 15 minutes per wash, followed by a single 20 minute wash in 0.1× SSC, 1% SDS at 45° C. The filters were then exposed to X-ray film at −70° C. for several days.

Plaques that hybridized with the labelled probe were purified by several rounds of replating and rescreening. Insert cDNAs were subcloned into the pBluescript SK(−) vector (Stratagene) by the in vivo excision method described by the manufacturer's protocol. Southern blots were performed in order to verify that the rescued cDNA hybridized to the PCR probe. Putative cGB-PDE cDNAs were sequenced using Sequenase® Version 2.0 (United States Biochemical Corporation, Cleveland, Ohio) or TaqTrack® kits (Promega).

Three distinct cDNA clones designated cGB-2, cGB-8 and cGB-10 were isolated. The DNA and deduced amino acid sequences of clone cGB-8 are set out in SEQ ID NOs: 9 and 10. The DNA sequence of cGB-10 is identical to the sequence of cGB-8 with the exception of one nucleotide. The DNA sequence of clone cGB-2 diverges from that of clone cGB-8 5' to nucleotide 219 of clone egb-8 (see SEQ ID NO: 9) and could encode a protein with a different amino terminus.

The cGB-8 cDNA clone is 4474 bp in length and contains a large open reading frame of 2625 bp. The triplet ATG at position 99–101 in the nucleotide sequence is predicted to be the translation initiation site of the cGB-PDE gene because it is preceded by an in-frame stop codon and the surrounding bases are compatible with the Kozak consensus initiation site for eucaryotic mRNAs. The stop codon TAG is located at positions 2724–2726, and is followed by 1748 bp of 3' untranslated sequence. The sequence of cGB-8 does not contain a transcription termination consensus sequence, therefore the clone may not represent the entire 3' untranslated region of the corresponding mRNA.

The open reading frame of the cGB-8 cDNA encodes an 875 amino acid polypeptide with a calculated molecular mass of 99.5 kD. This calculated molecular mass is only slightly larger than the reported molecular mass of purified cGB-PDE, estimated by SDS-PAGE analysis to be approximately 93 kDa. The deduced amino acid sequence of cGB-8 corresponded exactly to all peptide sequences obtained from purified bovine lung cGB-PDE providing strong evidence that cGB-8 encodes cGB-PDE.

EXAMPLE 2

A search of the SWISS-PROT and GEnEmbl data banks (Release of February, 1992) conducted using the FASTA program supplied with the Genetics Computer Group (GCG) Software Package (Madison, Wis.) revealed that only DNA and amino acid sequences reported for other PDEs displayed significant similarity to the DNA and deduced amino acid of clone cGB-8.

Pairwise comparisons of the cGB-PDE deduced amino acid sequence with the sequences of eight other PDEs were conducted using the ALIGN [Dayhoff et al., Methods Enzymol., 92: 524–545 (1983)] and BESTFIT [Wilbur et al., Proc. Natl. Acad. Sci. USA, 80: 726–730 (1983)] programs. Like all mammalian phosphodiesterases sequenced to date, cGB-PDE contains a conserved catalytic domain sequence of approximately 250 amino acids in the carboxyl-terminal half of the protein that is thought to be essential for catalytic activity. This segment comprises amino acids 578–812 of SEQ ID NO: 9 and exhibits sequence conservation with the corresponding regions of other PDEs. Table 1 below sets out the specific identity values obtained in pairwise comparisons of other PDEs with amino acids 578–812 of cGB-PDE, wherein "ratdunce" is the rat cAMP-specific PDE; "61 kCaM" is the bovine 61 kDa calcium/calmodulin-dependent PDE; "63 kCaM" is the bovine 63 kDa calcium/calmodulin-dependent PDE; "drosdunce" is the drosophila cAMP-specific dunce PDE; "ROS-α" is the bovine ROS-PDE α-subunit; "ROS-β" is the bovine ROS-PDE β-subunit; "COS-α" is the bovine COS-PDE α' subunit; and "cGs" is the bovine cGs-PDE (612–844).

TABLE 1

| Phosphodiesterase | Catalytic Domain Residues | % Identity |
| --- | --- | --- |
| Ratdunce | 77–316 | 31 |
| 61 kCaM | 193–422 | 29 |
| 63 kcam | 195–424 | 29 |
| drosdunce | 1–239 | 28 |
| ROS-α | 535–778 | 45 |
| ROS-β | 533–776 | 46 |
| COS-α' | 533–776 | 48 |
| cGs | 612–844 | 40 |

Multiple sequence alignments were performed using the Progressive Alignment Algorithm [Feng et al., Methods Enzymol., 183: 375–387 (1990)] implemented in the PILEUP program (GCG Software). FIGS. 1A–1C shows a multiple sequence alignment of the proposed catalytic domain of cGB-PDE with the all the corresponding regions of the PDEs of Table 1. Twenty-eight residues (see residues indicated by one letter amino acid abbreviations in the "conserved" line on FIGS. 1A–1C) are invariant among the isoenzymes including several conserved histidine residues predicted to play a functional role in catalysis. See Charbonneau et al., Proc. Natl. Acad. Sci. USA, supra. The catalytic domain of cGB-PDE more closely resembles the catalytic domains of the ROS-PDEs and COS-PDEs than the corresponding regions of other PDE isoenzymes. There are several conserved regions among the photoreceptor PDEs and cGB-PDE that are not shared by other PDEs. Amino acid positions in these regions that are invariant in the photoreceptor PDE and cGB-PDE sequences are indicated by stars in the "conserved" line of FIGS 2A–2C. Regions of homology among cGB-PDE and the ROS- and COS-PDEs may serve important roles in conferring specificity for cGMP hydrolysis relative to cAMP hydrolysis or for sensitivity to specific pharmacological agents.

Sequence similarity between cGB-PDE, cGs-PDE and the photoreceptor PDEs, is not limited to the conserved catalytic domain but also includes the noncatalytic cGMP binding domain in the amino-terminal half of the protein. Optimization of the alignment between cGB-PDE, cGs-PDE and the photoreceptor PDEs indicates that an amino-terminal conserved segment may exist including amino acids 142–526 of SEQ ID NO: 9. Pairwise analysis of the sequence of the proposed cGMP-binding domain of cGB-PDE with the corresponding regions of the photoreceptor PDEs and cGs-PDE revealed 26–28% sequence identity. Multiple sequence alignment of the proposed cGMP-binding domains with the cGMP-binding PDEs is shown in FIG. 2 wherein abbreviations are the same as indicated for Table 1. Thirty-eight positions in this non-catalytic domain appear to be invariant among all cGMP-binding PDEs (see positions indicated by one letter amino acid abbreviations in the "conserved" line of FIGS. 2A–2C).

The cGMP-binding domain of the cGMP-binding PDEs contains internally homologous repeats which may form two similar but distinct inter- or intra-subunit cGMP-binding sites. FIG. 3 shows a multiple sequence alignment of the repeats a (corresponding to amino acids 228–311 of cGB-PDE) and b (corresponding to amino acids 410–500 of cGB-PDE) of the cGMP-binding PDEs. Seven residues are invariant in each A and B regions (see residues indicated by one letter amino acid abbreviations in the "conserved" line of FIG. 3). Residues that are chemically conserved in the A and B regions are indicated by stars in the "conserved" line of FIG. 3. cGMP analog studies of cGB-PDE support the existence of a hydrogen bond between the cyclic nucleotide binding site on cGB-PDE and the 2'OH of cGMP.

Three regions of cGB-PDE have no significant sequence similarity to other PDE isoenzymes. These regions include the sequence flanking the carboxyl-terminal end of the catalytic domain (amino acids 812–875), the sequence separating the cGMP-binding and catalytic domains (amino acids 527–577) and the amino-terminal sequence spanning amino acids 1–141. The site (the serine at position 92 of SEQ ID NO: 10) of phosphorylation of cGB-PDE by cGK is located in this amino-terminal region of sequence. Binding of cGMP to the allosteric site on cGB-PDE is required for its phosphorylation.

A proposed domain structure of cGB-PDE based on the foregoing comparisons with other PDE isoenzymes is presented in FIG. 4. This domain structure is supported by the biochemical studies of cGB-PDE purified from bovine lung.

EXAMPLE 3

The presence of cGB-PDE mRNA in various bovine tissues was examined by Northern blot hybridization.

Polyadenylated RNA was purified from total RNA preparations using the Poly(A) Quick® mRNA purification kit (Stratagene) according to the manufacturer's protocol. RNA samples (5 µg) were loaded onto a 1.2% agarose, 6.7% formaldehyde gel. Electrophoresis and RNA transfer were performed as previously described in Sonnenburg et at., supra. Prehybridization of the RNA blot was carried out for 4 hours at 45° C. in a solution containing 50% formamide, 5× SSC, 25 mM sodium phosphate, pH 7, 2× Denhardt's solution, 10% dextran sulfate, and 0.1 mg/ml yeast tRNA. A random hexanucleotide-primer-labelled probe ($5 \times 10^8$ cpm/µg) was prepared as described in Feinberg et al., supra, using the 4.7 kb cGB-8 cDNA clone of Example 2 excised by digestion with AccI and SacII. The probe was heat denatured and injected into a blotting bag ($6 \times 10^5$ cpm/ml) following prehybridization. The Northern blot was hybridized overnight at 45° C., followed by one 15 minute wash with 2× SSC, 0.1% SDS at room temperature, and three 20 minute washes with 0.1× SSC, 0.1% SDS at 45° C. The blot was exposed to X-ray film for 24 hours at −70° C. The size of the RNA that hybridized with the cGB-PDE probe was estimated using a 0.24–9.5 kb RNA ladder that was stained with ethidium bromide and visualized with UV light.

The $^{32}$P-labelled cGB-PDE cDNA hybridized to a single 6.8 kb bovine lung RNA species. A mRNA band of the identical size was also detected in polyadenylated RNA isolated from bovine trachea, aorta, kidney and spleen.

EXAMPLE 4

The cGB-PDE cDNA in clone cGB-8 of Example 2 was expressed in COS-7 cells (ATCC CRL165 1).

A portion of the cGB-8 cDNA was isolated following digestion with the restriction enzyme XbaI. XbaI cut at a position in the pBluescript polylinker sequence located 30 bp upstream of the 5' end of the cGB-8 insert and at position 3359 within the cGB-8 insert. The resulting 3389 bp fragment, which contains the entire coding region of cGB-8, was then ligated into the unique XbaI cloning site of the expression vector pCDM8 (Invitrogen, San Diego, Calif.). The pCDM8 plasmid is a 4.5 kb eucaryotic expression vector containing a cytomegalovirus promoter and enhancer, an SV40-derived origin of replication, a polyadenylation signal, a procaryotic origin of replication (derived from pBR322) and a procaryotic genetic marker (supF). *E. coli* MC1061/P3 cells (Invitrogen) were transformed with the resulting ligation products, and transformation positive colonies were screened for proper orientation of the cGB-8 insert using PCR and restriction enzyme analysis. The resulting expression construct containing the cGB-8 insert in the proper orientation is referred to as pCDM8-cGB-PDE.

The pCDM8-cGB-PDE DNA was purified from large-scale plasmid preparations using Qiagen pack-500 columns (Chatsworth, Calif.) according to the manufacturer's protocol. COS-7 cells were cultured in Dulbecco's modified Eagle's medium (DMEM) containing 10% fetal bovine serum, 50 µg/ml penicillin and 50 µg/ml streptomycin at 37° C. in a humidified 5 % $CO_2$ atmosphere. Approximately 24 hours prior to transfection, confluent 100 mm dishes of cells were replated at one-fourth or one-fifth the original density. In a typical transfection experiment, cells were washed with buffer containing 137 mM NaCl, 2.7mM KCl, 1.1 mM potassium phosphate, and 8.1 mM sodium phosphate, pH 7.2 (PBS). Then 4–5 ml of DMEM containing 10% NuSerum (Collaborative Biomedical Products, Bedford, Mass.) was added to each plate. Transfection with 10 µg pCDM8-cGB-PDE DNA or pCDM8 vector DNA mixed with 400 µg DEAE-dextran (Pharmacia) in 60 µl TBS [Tris-buffered saline: 25 mM Tris-HCl (pH 7.4), 137 mM NaCl, 5 mM KCl, 0.6 mM $Na_2HPO_4$, 0.7 mM $CaCl_2$, and 0.5 mM $MgCl_2$] was carried out by dropwise addition of the mixture to each plate. The cells were incubated at 37 ° C., 5% $CO_2$ for 4 hours, and then treated with 10% dimethyl sulfoxide in PBS for 1 minute. After 2 minutes, the dimethyl sulfoxide was removed, the cells were washed with PBS and incubated in complete medium. After 48 hours, cells were suspended in 0.5–1 ml of cold homogenization buffer [40 mM Tris-HCl (pH 7.5), 15 mM benzamidine, 15 mM β-mercaptoethanol, 0.7 µg/ml pepstatin A, 0.5 µg/ml leupeptin, and 5 µM EDTA] per plate of cells, and disrupted using a Dounce homogenizer. The resulting whole-cell extracts were assayed for phosphodiesterase activity, cGMP-binding activity, and total protein concentration as described below in Example 5.

EXAMPLE 5

Phosphodiesterase activity in extracts of the transfected COS cells of Example 5 or in extracts of mock transfected COS cells was measured using a modification of the assay procedure described for the cGs-PDE in Martins et al., *J. Biol. Chem.*, 257: 1973–1979 (1982). Cells were harvested and extracts prepared 48 hours after transfection. Incubation mixtures contained 40 mM MOPS buffer (pH 7), 0.8 mM EDTA, 15 mM magnesium acetate, 2 mg/ml bovine serum albumin, 20 µM [$^3$H]cGMP or [$^3$H]cAMP (100,000–200,000 cpm/assay) and COS-7 cell extract in a total volume of 250 µl. The reaction mixture was incubated for 10 minutes at 30° C., and then stopped by boiling. Next, 10 µl of 10 mg/ml *Crotalus atrox* venom (Sigma) was added followed by a 10 minute incubation at 30° C. Nucleoside products were separated from unreacted nucleotides as described in Martins et al., supra. In all studies, less than 15% of the total [$^3$H]cyclic nucleotide was hydrolyzed during the reaction.

Figure 5:
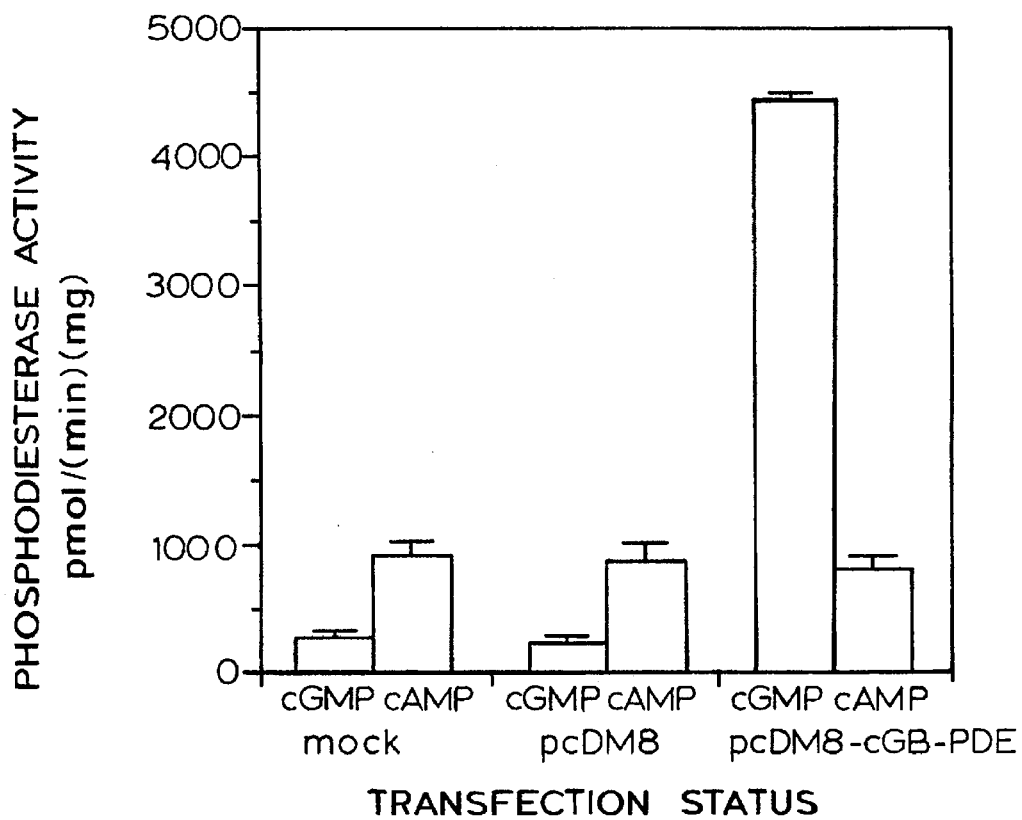
FIG. 5 is a bar graph representing the results of experiments in which extracts of COS cells transfected with bovine cGB-PDE sequences or extracts of untransfected COS cells were assayed for phosphodiesterase activity using either 20 μM cGMP or 20 μM cAMP as the substrate.

The results of the assays are presented in FIG. 5 wherein the results shown are averages of three separate transfections. Transfection of COS-7 cells with pCDM8-cGB-PDE DNA resulted in the expression of approximately 15-fold higher levels of cGMP phosphodiesterase activity than in mock-transfected cells or in cells transfected with pCDM8 vector alone. No increase in cAMP phosphodiesterase activity over mock or vector-only transfected cells was detected in extracts from cells transfected with pCDM8-cGB-PDE DNA. These results confirm that the cGB-PDE bovine cDNA encodes a cGMP-specific phosphodiesterase.

Extracts from the transfected COS cells of Example 4 were also assayed for cGMP PDE activity in the presence of a series of concentrations of the PDE inhibitors zaprinast, dipyridamole (Sigma), isobutyl-1-methyl-8-methoxymethylxanthine (MeOxMeMIX) and rolipram.

Figure 6:
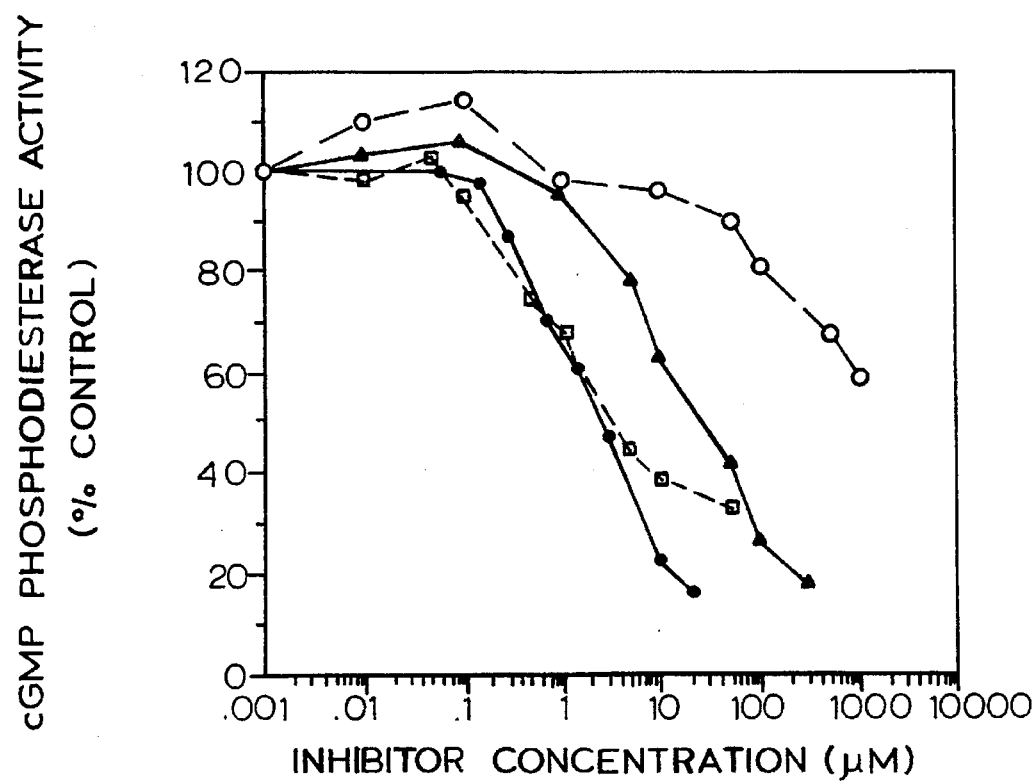
FIG. 6 is a graph depicting results of assays of extracts from cells transfected with bovine cGB-PDE sequences for cGMP phosphodiesterase activity in the presence of a series of concentrations of phosphodiesterase inhibitors including dypyridamole (closed squares), zaprinast (closed circles), methoxymethylxanthine (closed triangles) and rolipram (open circles)

The results of the assays are presented in FIG. 6 wherein PDE activity in the absence of inhibitor is taken as 100% and each data point represents the average of two separate determinations. The relative potencies of PDE inhibitors for inhibition of cGMP hydrolysis by the expressed cGB-BPDE cDNA protein product were identical to those relative potencies reported for native cGB-PDE purified from bovine lung (Thomas I, supra). $IC_{50}$ values calculated from the curves in FIG. 6 are as follows: zaprinast (closed circles), 2 µM; dipyridamole (closed squares), 3.5 µM; MeOxMeMIX (closed triangles), 30 µM; and rolipram (open circles), >300 µM. The $IC_{50}$ value of zaprinast, a relatively specific inhibitor of cGMP-specific phosphodiesterases, was at least two orders of magnitude lower than that reported for inhibition of phosphodiesterase activity of the cGs-PDE or of the cGMP-inhibited phosphodiesterase (cGi-PDEs) (Reeves et al., pp. 300–316 in Beavo et al., supra). Dipyrimadole, an effective inhibitor of selected cAMP- and cGMP-specific phosphodiesterases, was also a potent inhibitor of the expressed cGB-PDE. The relatively selective inhibitor of calcium/calmodulin-stimulated phosphodiesterase (CaM-PDEs), MeOxMeMIX, was approximately 10-fold less potent than zaprinast and dipyridamole, in agreement with results using cGB-PDE activity purified from bovine lung. Rolipram, a potent inhibitor of low $K_m$ cAMP phosphodisterases, was a poor inhibitor of expressed cGB-PDE cDNA protein product. These results show that the cGB-PDE cDNA encodes a phosphodiesterase that possesses catalytic activity characteristic of cGB-PDE isolated from bovine tissue, thus verifying the identity of the cGB-8 cDNA clone as a cGB-PDE.

It is of interest to note that although the relative potencies of the PDE inhibitors for inhibition of cGMP hydrolysis were identical for the recombinant and bovine isolate cGB-PDE, the absolute $IC_{50}$ values for all inhibitors tested were 2–7 fold higher for the recombinant cGB-PDE. This difference could not be attributed to the effects of any factors present in COS-7 cell extracts on cGMP hydrolytic activity, since cGB-PDE isolated from bovine tissue exhibited identical kinetics of inhibition as a pure enzyme, or when added back to extracts of mock-transfected COS-7 cells. This apparent difference in pharmacological sensitivity may be due to a subtle difference in the structure of the recombinant cGB-PDE cDNA protein product and bovine lung cGB-PDE, such as a difference in post-translational modification at or near the catalytic site. Alternatively, this difference may be due to an alteration of the catalytic activity of bovine lung cGB-PDE over several purification steps.

Cell extracts were assayed for [$^3$H]cGMP-binding activity in the absence or presence of 0.2 mM 3-isobutyl-1-methylxanthine (IBMX) (Sigma), a competitive inhibitor of cGMP hydrolysis. The cGMP binding assay, modified from the assay described in Thomas I, supra, was conducted in a total volume of 80 µl. Sixty µl of cell extract was combined with 20 µl of a binding cocktail such that the final concentration of components of the mixture were 1 µM [$^3$H]cGMP, 5 µM cAMP, and 10 µM 8-bromo-cGMP. The cAMP and 8-bromo-cGMP were added to block [$^3$H]cGMP binding to cAK and cGK, respectively. Assays were carried out in the absence and presence of 0.2 mM IBMX. The reaction was initiated by the addition of the cell extract, and was incubated for 60 minutes at 0° C. Filtration of the reaction mixtures was carried out as described in Thomas I, supra. Blanks were determined by parallel incubations with homogenization buffer replacing cell extracts, or with a 100-fold excess of unlabelled cGMP. Similar results were obtained with both methods. Total protein concentration of the cell extracts was determined by the method of Bradford, *Anal. Biochem.*, 72: 248–254 (1976) using bovine serum albumin as the standard.

Figure 7:
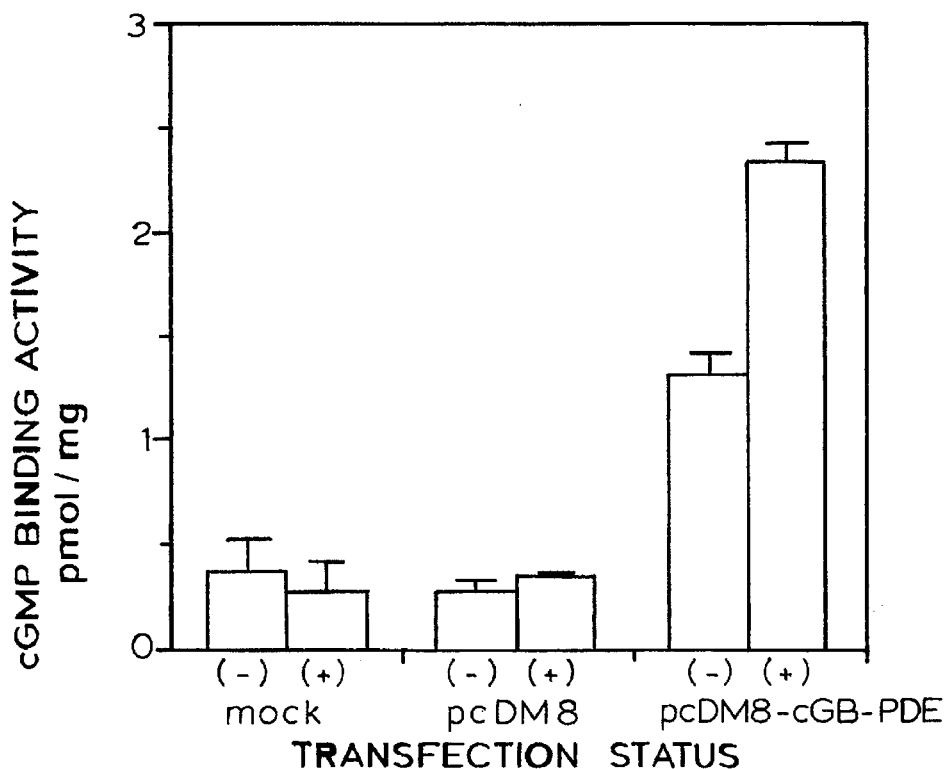
FIG. 7 is a bar graph presenting results of experiments in which cell extracts from COS cells transfected with bovine cGB-PDE sequences or control untransfected COS cells were assayed for [$^3$H]cGMP-binding activity in the absence (−) or presence (+) of 0.2 mM IBMX.

Results of the assay are set out in FIG. 7. When measured at 1 µM [$^3$H]cGMP in the presence of 0.2 mM IBMX, extracts from COS-7 cells transfected with pCDM8-cGB-PDE exhibited 8-fold higher cGMP-binding activity than extracts from mock-transfected cells. No IBMX stimulation of background cGMP binding was observed suggesting that little or no endogenous cGB-PDE was present in the COS-7 cell extracts. In extracts of pCDM8-cGB-PDE transfected cells cGMP-specific activity was stimulated approximately 1.8-fold by the addition of 0.2 mM IBMX. The ability of IBMX to stimulate cGMP binding 2–5 fold is a distinctive property of the cGMP-binding phosphodisterases.

Figure 8:
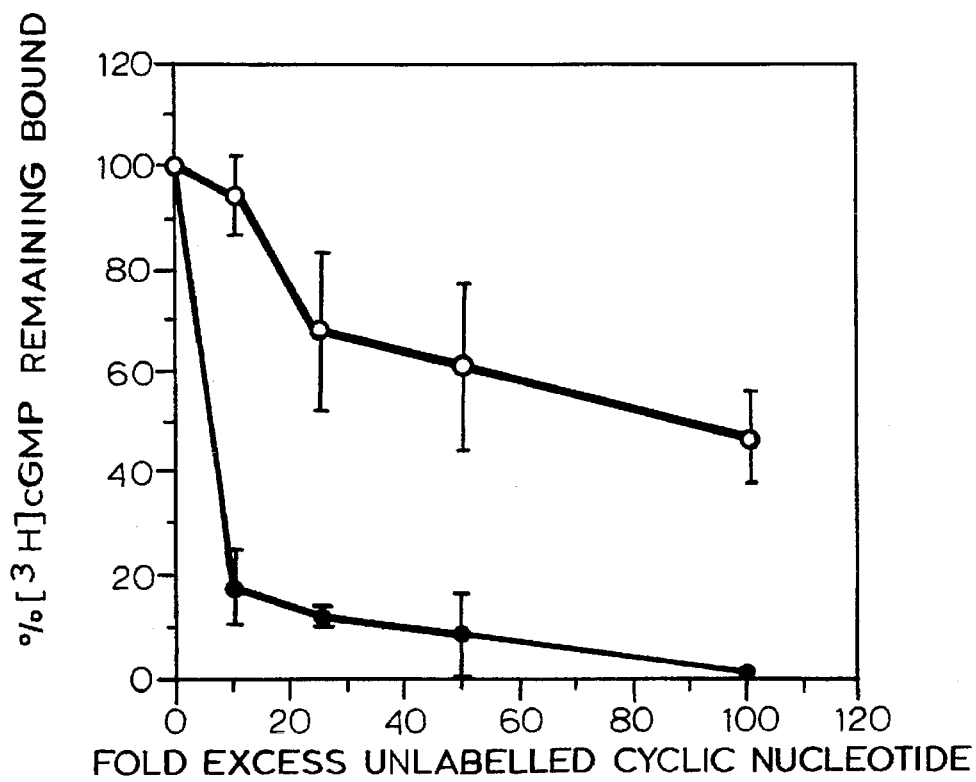
FIG. 8 is a graph of the results of assays in which extracts from cells transfected with bovine cGB-PDE sequences were assayed for [$^3$H]cGMP-binding activity in the presence of excess unlabelled cAMP (open circles) or cGMP (closed circles) at the concentrations indicated.

Cell extracts were assayed as described above for [$^3$H] cGMP-binding activity (wherein concentration of [$^3$H] cGMP was 2.5 µM) in the presence of excess unlabelled cAMP or cGMP. Results are presented in FIG. 8 wherein cGMP binding in the absence of unlabelled competitor was taken as 100% and each data point represents the average of three separate determinations. The binding activity of the protein product encoded by the cGB-PDE cDNA was specific for cGMP relative to cAMP. Less than 10-fold higher concentrations of unlabelled cGMP were required to inhibit [$^3$H]cGMP binding activity by 50% whereas approximately 100-fold higher concentrations of cAMP were required for the same degree of inhibition.

The results presented in this example show that the cGB-PDE cDNA encodes a phosphodiesterase which possesses biochemical activities characteristic of native cGB-PDE.

EXAMPLE 6

Several human cDNA clones, homologous to the bovine cDNA clone encoding cGB-PDE, were isolated by hybridization under stringent conditions using a nucleic acid probe corresponding to a portion of the bovine cGB-8 clone (nucleotides 489–1312 of SEQ ID NO: 9).

Isolation of cDNA Fragments Encoding Human cGB-PDE

Three human cDNA libraries (two glioblastoma and one lung) in the vector lambda Zap were probed with the bovine cGB-PDE sequence. The PCR-generated clone corresponding to nucleotides 484–1312 of SEQ ID NO: 9 which is described in Example 1 was digested with EcoRI and SalI and the resulting 0.8 kb cDNA insert was isolated and purified by agarose gel electrophoresis. The fragment was labelled with radioactive nucleotides using a random primed DNA labelling kit (Boehringer).

The cDNA libraries were plated on 150 mm petri plates at a density of approximately 50,000 plaques per plate. Duplicate nitrocellulose filter replicas were prepared. The prehybridization buffer was 3× SSC, 0.1% sarkosyl, 10× Denhardt's, 20 mM sodium phosphate (pH 6.8) and 50 µg/ml salmon testes DNA. Prehybridization was carried out at 65° C. for a minimum of 30 minutes. Hybridization was carried out at 65° C. overnight in buffer of the same composition with the addition of 1–5×10$^5$ cpm/ml of probe. The filters were washed at 65° C. in 2× SSC, 0.1% SDS. Hybridizing plaques were detected by autoradiography. The number of cDNAs that hybridized to the bovine probe and the number of cDNAs screened are indicated in Table 2 below.

TABLE 2

| cDNA Library | Type | Positive Plaques | Plaques Screened |
| --- | --- | --- | --- |
| Human SW 1088 glioblastoma | dT-primed | 1 | 1.5 × 10$^6$ |
| Human lung | dT-primed | 2 | 1.5 × 10$^6$ |
| Human SW 1088 gliobastoma | dT-primed | 4 | 1.5 × 10$^6$ |

Plasmids designated cgbS2.1, cgbS3.1, cgbL23.1, cgbL27.1 and cgbS27.1 were excised in vivo from the lambda Zap clones and sequenced.

Clone cgbS3.1 contains 2060 bp of a PDE open reading frame followed by a putative intron. Analysis of clone cgbS2.1 reveals that it corresponds to clone cgbS3.1 positions 664 to 2060 and extends the PDE open reading frame an additional 585 bp before reading into a putative intron. The sequences of the putative 5' untranslated region and the protein encoding portions of the cgbS2.1 and cgbS3.1 clones are set out in SEQ ID NOs: 11 and 12, respectively. Combining the two cDNAs yields a sequence containing approximately 2.7 kb of an open reading encoding a PDE. The three other cDNAs did not extend any further 5' or 3' than cDNA cgbS3.1 or cDNA cgbS2.1.

To isolate additional cDNAs, probes specific for the 5' end of clone cgbS3.1 and the 3' end of clone cgbS2.1 were prepared and used to screen a SW1088 glioblastoma cDNA library and a human aorta cDNA library. A 5' probe was derived from clone cgbS3.1 by PCR using the primers cgbS3.1S311 and cgbL23.1A1286 whose sequences are set out in SEQ ID NOs: 8 and 9, respectively, and below.

Primer cgbS3.1S311 (SEQ ID NO: 13)

5' GCCACCAGAGAAATGGTC 3'

Primer cgbL23.1A1286 (SEQ ID NO: 14)

5' ACAATGGGTCTAAGAGGC 3'

The PCR reaction was carried out in a 50 ul reaction volume containing 50 pg cgbS3.1 cDNA, 0.2mM dNTP, 10 ug/ml each primer, 50 mM KCl, 10mM Tris-HCl pH 8.2, 1.5 mM MgCl$_2$ and Taq polymerase. After an initial four minute denaturation at 94° C., 30 cycles of one minute at 94° C., two minutes at 50° C. and four minutes at 72° C. were carried out. An approximately 0.2 kb fragment was generated by the PCR reaction which corresponded to nucleotides 300–496 of clone cgbS3.1.

A 3' probe was derived from cDNA cgbS2.1 by PCR using the oligos cgbL23.1S1190 and cgbS2.1A231 whose sequences are set out below.

Primer cgbL23.1S1190 (SEQ ID NO: 15)

5' TCAGTGCATGTTTGCTGC 3'

Primer cgbS2.1A231 (SEQ ID NO: 16)

5' TACAAACATGTTCATCAG 3'

The PCR reaction as carried out similarly to that described above for generating the 5' probe, and yielded a fragment of approximately 0.8 kb corresponding to nucleotides 1358–2139 of cDNA cgbS2.1. The 3' 157 nucleotides of the PCR fragment (not shown in SEQ ID NO: 12) are within the presumptive intron.

The two PCR fragments were purified and isolated by agarose gel electrophoresis, and were labelled with radioactive nucleotides by random priming. A random-primed SW1088 glioblastoma cDNA library (1.5×10$^6$ plaques) was screened with the labelled fragments as described above, and 19 hybridizing plaques were isolated. An additional 50 hybridizing plaques were isolated from a human aorta cDNA library (dT and random primed, Clontech, Palo Alto, Calif.).

Plasmids were excised in vivo from some of the positive lambda Zap clones and sequenced. A clone designated cgbS53.2, the sequence of which is set out in SEQ ID NO: 17, contains an approximately 1.1 kb insert whose sequence overlaps the last 61 bp of cgbS3.1 and extends the open reading frame an additional 135 bp beyond that found in cgbS2.1. The clone contains a termination codon and approximately 0.3 kB of putative 3' untranslated sequence.

Generation Of a Composite cDNA Encoding Human cGB-PDE

Clones cgbS3.1, cgbS2.1 and cgbS53.2 were used as described in the following paragraphs to build a composite cDNA that contained a complete human cGB-PDE opening reading frame. The composite cDNA is designated cgbmet156-2 and was inserted in the yeast ADH1 expression vector pBNY6N.

First, a plasmid designated cgb stop-2 was generated that contained the 3' end of the cGB-PDE open reading frame. A portion of the insert of the plasmid was generated by PCR using clone cgbS53.2 as a template. The PCR primers utilized were cgbS2.1S1700 and cgbstop-2.

Primer cgbS2.1S1700 (SEQ ID NO: 18)

5' TTTGGAAGATCCTCATCA 3'

Primer cgbstop-2 (SEQ ID NO: 19)

5' ATGTCTCGAGTCAGTTCCGCTTGGCCTG 3'

The PCR reaction was carried out in 50 ul containing 50 pg template DNA, 0.2 mM dNTPs, 20 mM Tris-HCl pH 8.2, 10 mM KCl, 6 mM (NH$_4$)$_2$SO$_4$, 1.5 mM MgCl$_2$, 0.1% Triton-X-100, 500 ng each palmer and 0.5 units of Pfu polymerase (Stratagene). The reaction was heated to 94° C. for 4 minutes and then 30 cycles of 1 minute at 94° C., 2 minutes at 50° C. and four minutes at 72° C. were performed. The polymerase was added during the first cycle at 50° C. The resulting PCR product was phenol/chloroform extracted, chloroform extracted, ethanol precipitated and cut with the restriction enzymes BclI and XhoI. The restriction fragment was purified on an agarose gel and eluted.

This fragment was ligated to the cDNA cgbS2.1 that had been grown in dam$^-$ E. coli, cut with the restriction enzymes BclI and XhoI, and gel-purified using the Promega magic PCR kit. The resulting plasmid was sequenced to verify that cgbstop-2 contains the 3' portion of the cGB-PDE open reading frame.

Second, a plasmid carrying the 5' end of the human cGB-PDE open reading frame was generated. Its insert was generated by PCR using clone cgbS3.1 as a template. PCR was performed as described above using primers cgbmet156 and cgbS2.1 A2150.

Primer cgbmet156 (SEQ ID NO: 20)

5' TACAGAATYCTGACCATGGAGCGGGCCGGC 3'

Primer cgbS2.1A2150 (SEQ ID NO: 21)

5' CATTCTAAGCGGATACAG 3'

The resulting PCR fragment was phenol/choloform extracted, choloform extracted, ethanol precipitated and purified on a Sepharose CL-6B column. The fragment was cut with the restriction enzymes EcoRV and EcoRI, run on an agarose gel and purified by spinning through glass wool. Following phenol/chloroform extraction, chloroform extraction and ethanol precipitation, the fragment was ligated into EcoRI/EcoRV digested BluescriptII SK(+) to generate plasmid cgbmet156. The DNA sequence of the insert and junctions was determined. The insert contains a new EcoRI site and an additional 5 nucleotides that together replace the original 155 nucleotides 5' of the initiation codon. The insert extends to an EcoRV site beginning 531 nucleotides from the initiation codon.

The 5' and 3' portions of the cGB-PDE open reading frame were then assembled in vector pBNY6a. The vector pBNY6a was cut with EcoRI and XhoI, isolated from a gel and combined with the agarose gel purified EcoRI/EcoRV fragment from cgbmet156 and the agarose gel purified EcoRV/XhoI fragment from cgbstop-2. The junctions of the insert were sequenced and the construct was named hcbgmet156-2 6a.

The cGB-PDE insert from hcbgmet156-2 6a was then moved into the expression vector pBNY6n. Expression of DNA inserted in this vector is directed from the yeast ADH1 promoter and terminator. The vector contains the yeast 2 micron origin of replication, the pUC19 origin of replication and an ampicillan resistance gene. Vector pBNY6n was cut with EcoRI and XhoI and gel-purified. The EcoRI/XhoI insert from hcgbmet156-2 6a was gel purified using Promega magic PCR columns and ligated into the cut pBNY6n. All new junctions in the resulting construct, hcgbmet156-2 6n, were sequenced. The DNA and deduced amino acid sequences of the insert of hcgbmet156-2 6n which encodes a composite human cGB-PDE is set out in SEQ ID NOs: 22 and 23. The insert extends from the first methionine in clone cgbS3.1 (nucleotide 156) to the stop codon (nucleotide 2781) in the composite cDNA. Because the methionine is the most 5' methionine in clone cgbS3.1 and because there are no stop codons in frame with the methionine and upstream of it, the insert in pBNY6n may represent a truncated form of the open reading frame.

Variant cDNAs

Four human cGB-PDE cDNAs that are different from the hcgbmet156-2 6n composite cDNA have been isolated. One cDNA, cgbL23.1, is missing an internal region of hcgbmet156-2 6n (nucleotides 997–1000 to 1444–1447). The exact end points of the deletion cannot be determined from the cDNA sequence at those positions. Three of the four variant cDNAs have 5' end sequences that diverge from the hcgbmet156-2 6n sequence upstream of nucleotide 151 (cDNAs cgbA7f, cgbA5C, cgbI2). These cDNAs presumably represent alteratively spliced or unspliced mRNAs.

EXAMPLE 7

The composite human cGB-PDE cDNA construct, hcgbmet156-2 6n, was transformed into the yeast strain YKS45 (ATCC 74225) (MATα his3 trp1 ura3 leu3 pde1::HIS3 pde2::TRP1) in which two endogenous PDE genes are deleted. Transformants complementing the leu⁻ deficiency of the YKS45 strain were selected and assayed for cGB-PDE activity. Extracts from cells bearing the plasmid hcgbmet156-2 6n were determined to display cyclic GMP-specific phosphodiesterase activity by the assay described below.

One liter of YKS45 cells transformed with the plasmid cgbmet156-2 6n and grown in SC-leu medium to a density of $1–2\times 10^7$ cells/ml was harvested by centrifugation, washed once with deionized water, frozen in dry ice/ethanol and stored at −70° C. Cell pellets (1–1.5 ml) were thawed on ice in the presence of an equal volume of 25 mM Tris-Cl (pH 8.0)/5 mM EDTA/5 mM EGTA/1 mM o-phenanthroline/0.5 mM AEBSF (Calbiochem)/0.1% β-mercaptoethanol and 10 ug/ml each of aprotinin, leupeptin, and pepstatin A. The thawed cells were added to 2 ml of acid-washed glass beads (425–600 μM, Sigma) in 15 ml Corex tube. Cells were broken with 4 cycles consisting of a 30 second vortexing on setting 1 followed by a 60 second incubation on ice. The cell lysate was centrifuged at 12,000 ×g for 10 minutes and the supernatant was passed through a 0.8 μ filter. The supernatant was assayed for cGMP PDE activity as follows. Samples were incubated for 20 minutes at 30° C. in the presence of 45 mM Tris-Cl (pH 8.0), 2 mM EGTA, 1 mM EDTA, 0.2mg/ml BSA, 5 mM $MgCl_2$, 0.2 mM o-phenanthroline, 2 ug/ml each of pepstatin A, leupeptin, and aprotinin, 0.1 mM AEBSF, 0.02% β-mercaptoethanol and 0.1 mM [$^3$H]cGMP as substrate. [$^{14}$C]-AMP (0.5 nCi/assay) was added as a recovery standard. The reaction was terminated with stop buffer (0.1M ethanolamine pH 9.0, 0.5M ammonium sulfate, 10 mM EDTA, 0.05 % SDS final concentration). The product was separated from the cyclic nucleotide substrate by chromatography on BioRad Affi-Gel 601. The sample was applied to a column containing approximately 0.25 ml of Affi-Gel 601 equilibrated in column buffer (0.1M ethanolamine pH 9.0 containing 0.5M ammonium sulfate). The column was washed five times with 0.5 ml of column buffer. The product was eluted with four 0.5 ml aliquots of 0.25 acetic acid and mixed with 5 ml Ecolume (ICN Biochemicals). The radioactive product was measured by scintillation counting.

EXAMPLE 8

Analysis of expression of cGB-PDE mRNA in human tissues was carried out by RNase protection assay.

A probe corresponding to a portion of the putative cGMP binding domain of cGB-PDE (402 bp corresponding to nucleotides 1450 through 1851 of SEQ ID NO: 13) was generated by PCR. The PCR fragment was inserted into the EcoRI site of the plasmid pBSII SK(−) to generate the plasmid RP3. RP3 plasmid DNA was linearized with XbaI and antisense probes were generated by a modification of the Stratagene T7 RNA polymeruse kit. Twenty-five ng of linearized plasmid was combined with 20 microcuries of alpha $^{32}$P rUTP (800 Ci/mmol, 10 mCi/ml), 1× transcription buffer (40 mM TrisCl, pH 8, 8 mM $MgCl_2$, 2 mM spermidine, 50 mM NaCl), 0.25 mM each rATP, rGTP and rCTP, 0.1 units of RNase Block II, 5 mM DTF, 8 μM rUTP and 5 units of T7 RNA Polymerase in a total volume of 5 μl. The reaction was allowed to proceed 1 hour at room temperature and then the DNA template was removed by digestion with RNase free DNase. The reaction was diluted into 100 μl of 40 mM TrisCl, pH 8, 6 mM $MgCl_2$ and 10 mM NaCl. Five units of RNase-free DNase were added and the reaction was allowed to continue another 15 minutes at 37° C. The reaction was stopped by a phenol extraction followed by a phenol chloroform extraction. One half volume of 7.5M $NH_4OAc$ was added and the probe was ethanol precipitated.

The RNase protection assays were carried out using the Ambion RNase Protection kit (Austin, Tex.) and 10 μg RNA isolated from human tissues by an acid guanidinium extraction method. Expression of cGB-PDE mRNA was easily detected in RNA extracted from skeletal muscle, uterus, bronchus, skin, right saphenous vein, aorta and SW1088 glioblastoma cells. Barely detectable expression was found in RNA extracted from right atrium, right ventricle, kidney cortex, and kidney medulla. Only complete protection of the RP3 probe was seen. The lack of partial protection argues against the cDNA cgbL23.1 (a variant cDNA described in Example 7) representing a major transcript, at least in these RNA samples.

EXAMPLE 9

Polyclonal antisera was raised to *E. coli*-produced fragments of the human cGB-PDE.

A portion of the human cGB-PDE cDNA (nucleotides 1668–2612 of SEQ ID NO: 22, amino acids 515–819 of SEQ ID NO: 23) was amplified by PCR and inserted into the *E. coli* expression vector pGEX2T (Pharmacia) as a BamHI/EcoRI fragment. The pGEX2T plasmid carries an ampicillin resistance gene, an *E. coli* laq I$^q$ gene and a portion of the *Schistosoma japonicum* glutathione-S-transferase (GST) gene. DNA inserted in the plasmid can be expressed as a fusion protein with GST and can then be cleaved from the GST portion of the protein with thrombin. The resulting plasmid, designated cgbPE3, was transformed into *E. coli* strain LE392 (Stratagene). Transformed cells were grown at 37° C. to an OD600 of 0.6. IPTG (isopropylthioalactopyranoside) was added to 0.1 mM and the cells were grown at 37° C. for an additional 2 hours. The cells were collected by centrifugation and lysed by sonication. Cell debris was removed by centrifugation and the supernatant was fractionated by SDS-PAGE. The gel was stained with cold 0.4M KCl and the GST-cgb fusion protein band was excised and electroeluted. The PDE portion of the protein was separated from the GST portion by digestion with thrombin. The digest was fractionated by SDS-PAGE, the PDE protein was electroeluted and injected subcutaneously into a rabbit. The resultant antisera recognizes both the bovine cGB-PDE fragment that was utilized as antigen and the full length human cGB-PDE protein expressed in yeast (see Example 8).

EXAMPLE 10

Developing modulators of the biological activities of specific PDEs requires differentiating PDE isozymes present in a particular assay preparation. The classical enzymological approach of isolating PDEs from natural tissue sources and studying each new isozyme is hampered by the limits of purification techniques and the inability to definitively assess whether complete resolution of a isozyme has been achieved. Another approach has been to identify assay conditions which might favor the contribution of one isozyme and minimize the contribution of others in a preparation. Still another approach has been the separation of PDEs by immunological means. Each of the foregoing approaches for differentiating PDE isozymes is time consuming and technically difficult. As a result many attempts to develop selective PDE modulators have been performed with preparations containing more than one isozyme. Moreover, PDE preparations from natural tissue sources are susceptible to limited proteolysis and may contain mixtures of active proteolytic products that have different kinetic, regulatory and physiological properties than the full length PDEs.

Recombinant cGB-PDE polypeptide products of the invention greatly facilitate the development of new and specific cGB-PDE modulators. The use of human recombinant enzymes for screening for modulators has many inherent advantages. The need for purification of an isozyme can be avoided by expressing it recombinantly in a host cell that lacks endogenous phosphodiesterase activity (e.g., yeast strain YKS45 deposited as ATCC 74225). Screening compounds against human protein avoids complications that often arise from screening against non-human protein where a compound optimized on a non-human protein may fail to be specific for or react with the human protein. For example, a single amino acid difference between the human and rodent $5HT_{1B}$ serotonin receptors accounts for the difference in binding of a compound to the receptors. [See Oskenberg et al., *Nature*, 360: 161–163 (1992)]. Once a compound that modulates the activity of the cGB-PDE is discovered, its selectivity can be evaluated by comparing its activity on the cGB-PDE to its activity on other PDE isozymes. Thus, the combination of the recombinant cGB-PDE products of the invention with other recombinant PDE products in a series of independent assays provides a system for developing selective modulators of cGB-PDE. Selective modulators may include, for example, antibodies and other proteins or peptides which specifically bind to the cGB-PDE or cGB-PDE nucleic acid, oligonucleotides which specifically bind to the cGB-PDE (see Patent Cooperation Treaty International Publication No. WO93/05182 published Mar. 18, 1993 which describes methods for selecting oligonucleotides which selectively bind to target biomolecules) or cGB-PDE nucleic acid (e.g., antisense oligonucleotides) and other non-peptide natural or synthetic compounds which specifically bind to the cGB-PDE or cGB-PDE nucleic acid. Mutant forms of the cGB-PDE which alter the enzymatic activity of the cGB-PDE or its localization in a cell are also contemplated. Crystallization of recombinant cGB-PDE alone and bound to a modulator, analysis of atomic structure by X-ray crystallography, and computer modelling of those structures are methods useful for designing and optimizing non-peptide selective modulators. See, for example, Erickson et al., *Ann. Rep. Med. Chem.*, 27: 271–289 (1992) for a general review of structure-based drug design.

Targets for the development of selective modulators include, for example: (1) the regions of the cGB-PDE which contact other proteins and/or localize the cGB-PDE within a cell, (2) the regions of the cGB-PDE which bind substrate, (3) the allosteric cGMP-binding site(s) of cGB-PDE, (4) the metal-binding regions of the cGB-PDE, (5) the phosphorylation site(s) of cGB-PDE and (6) the regions of the cGB-PDE which are involved in dimerization of cGB-PDE subunits.

While the present invention has been described in terms of specific embodiments, it is understood that variations and modifications will occur to those skilled in the art. Accordingly, only such limitations as appear in the appended claims should be placed on the invention

---

We claim:

1. A purified and isolated polynucleotide encoding the cyclic GMP binding phosphodiesterase (cGB-PDE) polypeptide set out in SEQ ID NO: 10 or 23.

2. The polynucleotide of claim 1 which is a DNA.

3. The DNA of claim 2 which is a cDNA.

4. The DNA of claim 2 which is a genomic DNA.

5. An RNA transcript of the DNA of claim 2.

6. The DNA of claim 4 further comprising an endogenous expression control DNA sequence.

7. A vector comprising a DNA according to claim 2.

8. The vector of claim 7 wherein said DNA is operatively linked to an expression control sequence.

9. A host cell stably transformed or transfected with a DNA sequence according to claim 2 in a manner allowing the expression in said host cell of the cGB-PDE of SEQ ID NO: 10 or 23.

10. A method of producing a cGB-PDE polypeptide, said method comprising growing a host cell according to claim 9 in a suitable nutrient medium and isolating cGB-PDE polypeptide from said cell or the medium of its growth.

11. A purified and isolated polynucleotide selected from the group consisting of a polynucleotide encoding an allelic variant of the cGB-PDE polypeptide set out in SEQ ID NO: 23 and a polynucleotide encoding a non-human species cGB-PDE homolog, wherein said polynucleotide hybridizes at about 65° C. in 3× SSC, 20 mM sodium phosphate pH 6.8, with washing at about 65° C. in 2× SSC to the non-coding strand of the DNA set out in SEQ ID NO: 22.

12. A purified and isolated polynucleotide comprising the DNA sequence set out SEQ ID NO: 9 or 22.

* * * * *

UNITED STATES PATENT AND TRADEMARK OFFICE
CERTIFICATE OF CORRECTION

PATENT NO.   : 5,652,131
DATED         : July 29, 1997
INVENTOR(S)  : Beavo et al.

It is certified that error appears in the above-identified patent and that said Letters Patent is hereby corrected as shown below:

Title page,
OTHER PUBLICATIONS, Murray *et al.*, replace "Phosphodiesleases" with -- Phosphodiesterases --.
Sonnenburg *et al.*, replace "Phosphodieterase" with -- Phosphodiesterase --.
M.P. Deutscher, replace "Enzeymol" with -- Enzymol --.

Column 1,
Line 57, replace "specfic" with -- specific --.

Column 2,
Line 23, replace "at" with -- α --.
Line 49, replace "Hamer" with -- Hamet --.

Column 3,
Line 6, replace "at." with -- al. --.
Line 19, replace "at." with -- al. --.

Column 5,
Line 21, replace "isloated" with -- isolated --.

Column 7,
Line 13, replace "supra, or was" with -- supra, was --.

Column 10,
Line 62, replace "egb-8" with -- cGB-8 --.

Column 12,
Line 1, replace "with the all" with -- with all --.

Column 13,
Line 9, replace "at." with -- al. --.

Column 16,
Line 3, replace "phosphodisterases" with -- phosphodiesterases --.

UNITED STATES PATENT AND TRADEMARK OFFICE
CERTIFICATE OF CORRECTION

PATENT NO.   : 5,652,131
DATED        : July 29, 1997
INVENTOR(S)  : Beavo et al.

It is certified that error appears in the above-identified patent and that said Letters Patent is hereby corrected as shown below:

Column 18,
Line 9, replace "5' ATGTCTCGAGTCAGTTCCGCTrGGCCTG 3'" with
-- 5' ATGTCTCGAGTCAGTTCCGCTGGCCTG 3' --.
Line 13, replace "palmer" with -- primer --.
Line 34, replace "5' TACAGAATYCTGACCATGGAGCGGGCCGGC 3'" with
-- 5' TACAGAATTCTGACCATGGAGCGGGCCGGC 3' --.
Line 38, replace "choloform" with -- chloroform --.
Line 39, replace "choloform" with -- chloroform --.

Column 20,
Line 16, replace "polymeruse" with -- polymerase --.

Column 22,
Line 44, replace "invention" with -- invention. --.

Column 58,
Line 2, replace "out SEQ" with -- out in SEQ --.

Signed and Sealed this

Tenth Day of December, 2002

JAMES E. ROGAN
*Director of the United States Patent and Trademark Office*